(12) United States Patent　　(10) Patent No.: US 9,339,487 B2
Miyajima et al.　　(45) Date of Patent: May 17, 2016

(54) DRY POWDER PHARMACEUTICAL COMPOSITION FOR INHALATION

(75) Inventors: Makoto Miyajima, Tokyo (JP); Shigeru Noda, Tokyo (JP); Kazuhiro Inoue, Tokyo (JP); Michiko Kumon, Tokyo (JP); Katsuyasu Ishida, Kanagawa (JP); Hitoshi Ishizuka, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 188 days.

(21) Appl. No.: 13/132,599

(22) PCT Filed: Dec. 24, 2009

(86) PCT No.: PCT/JP2009/071380
§ 371 (c)(1),
(2), (4) Date: Jun. 2, 2011

(87) PCT Pub. No.: WO2010/074113
PCT Pub. Date: Jul. 1, 2010

(65) Prior Publication Data
US 2011/0256188 A1　Oct. 20, 2011

(30) Foreign Application Priority Data

Dec. 24, 2008　(JP) ................... 2008-328006
Nov. 5, 2009　(JP) ................... 2009-253610

(51) Int. Cl.
*A61K 31/351*　(2006.01)
*A61K 9/14*　(2006.01)
*A61P 31/16*　(2006.01)
*C07D 309/28*　(2006.01)
*A61K 9/00*　(2006.01)

(52) U.S. Cl.
CPC ............. *A61K 31/351* (2013.01); *A61K 9/0075* (2013.01); *Y10T 428/2982* (2015.01)

(58) Field of Classification Search
CPC ............... A61K 9/0075; A61K 31/351; Y10T 428/2981
See application file for complete search history.

(56) References Cited

U.S. PATENT DOCUMENTS

| | | | |
|---|---|---|---|
| 5,478,578 A | 12/1995 | Arnold et al. | |
| 5,952,375 A | 9/1999 | Bischofberger et al. | |
| 6,340,702 B1 | 1/2002 | Honda et al. | |
| 6,844,363 B2 | 1/2005 | Murakami et al. | |
| 2007/0202053 A1* | 8/2007 | Bilzi et al. ................... | 424/46 |
| 2008/0063722 A1 | 3/2008 | Ward et al. | |

FOREIGN PATENT DOCUMENTS

| | | |
|---|---|---|
| JP | 2001-151673 A | 6/2001 |
| JP | 2002-012555 | 1/2002 |
| JP | 2002012555 * | 1/2002 |
| JP | 2004500424 A | 1/2004 |
| JP | 2004510806 A | 4/2004 |
| JP | 2005504774 A | 2/2005 |
| JP | 2005505534 A | 2/2005 |
| JP | 4205314 B2 | 1/2009 |
| JP | 2009197025 A | 9/2009 |
| WO | WO 91/16320 | 10/1991 |

(Continued)

OTHER PUBLICATIONS

Xian Ming Zeng et al, "Effects of particle size and adding sequence of fine lactose on the deposition of salbutamol sulphate from a dry powder formulation", International Journal of Pharmaceutics, 1999, vol. 182, pp. 133-144.

(Continued)

*Primary Examiner* — Suzanne Ziska
*Assistant Examiner* — Thurman Wheeler
(74) *Attorney, Agent, or Firm* — Holtz, Holtz & Volek PC

(57) ABSTRACT

There is provided a dry powder pharmaceutical composition for inhalation useful for preventing and/or treating influenza virus infections contains as a medicinal component a compound represented by formula (I):

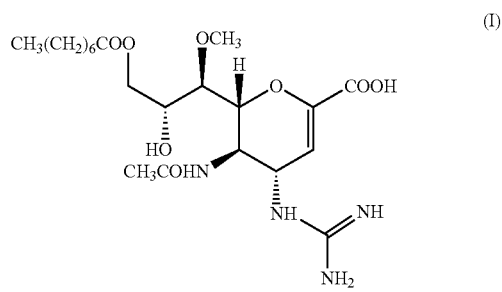

and optionally a compound represented by formula (II):

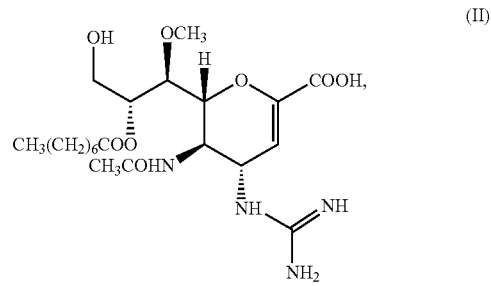

a pharmacologically acceptable salt thereof, or a hydrate thereof.

20 Claims, 1 Drawing Sheet

(56) References Cited

FOREIGN PATENT DOCUMENTS

| WO | 0178696 A2 | 10/2001 |
|---|---|---|
| WO | WO 01/80892 A1 | 11/2001 |
| WO | 0230390 A2 | 4/2002 |
| WO | 03017970 A1 | 3/2003 |
| WO | 03017979 A1 | 3/2003 |

OTHER PUBLICATIONS

Fridrun Podczeck, "The relationship between physical properties of lactose monohydrate and the aerodynamic behaviour of adhered drug particles", International Journal of Pharmaceutics, 1998, vol. 160, pp. 119-130.

Pieter Zanen et al, "Optimal particle size for $\beta_2$ agonist and anticholinergic aerosols in patients with severe airflow obstruction", Thorax, 1996, 51, pp. 977-980.

Bo Olsson et al, "Effect of inlet throat on the correlation between measured fine particle dose and lung deposition", Interpharm Press, 1996, pp. 273-281.

J.N. Staniforth et al, "Interparticle forces in binary and ternary ordered powder mixes", J. Pharm. Pharmacol., 1982, 34, pp. 141-145.

J.A. Hersey, "Ordered Mixing: a New Concept in Powder Mixing Practice", Powder Technology, 1975, 11, pp. 41-44.

David A. Edwards et al, "Large Porous Particles for Pulmonary Drug Delivery", Science, 1997, vol. 276, pp. 1868-1871.

"Review of Antivirals for Home Stockpiling Use for Pandemic Influenza and Development Plan for Relenza MedKit", FDA Antiviral Drug Products and Nonprescription Drug Products Advisory Committee Meeting, Jan. 1, 2008, pp. 1-91, XP007922678.

Supplementary European Search Report for EP 09 83 4911 mailed May 26, 2014.

Japanese Office Action (and English translation thereof) dated Oct. 11, 2013, issued in counterpart Japanese Application No. 2010-544095.

* cited by examiner

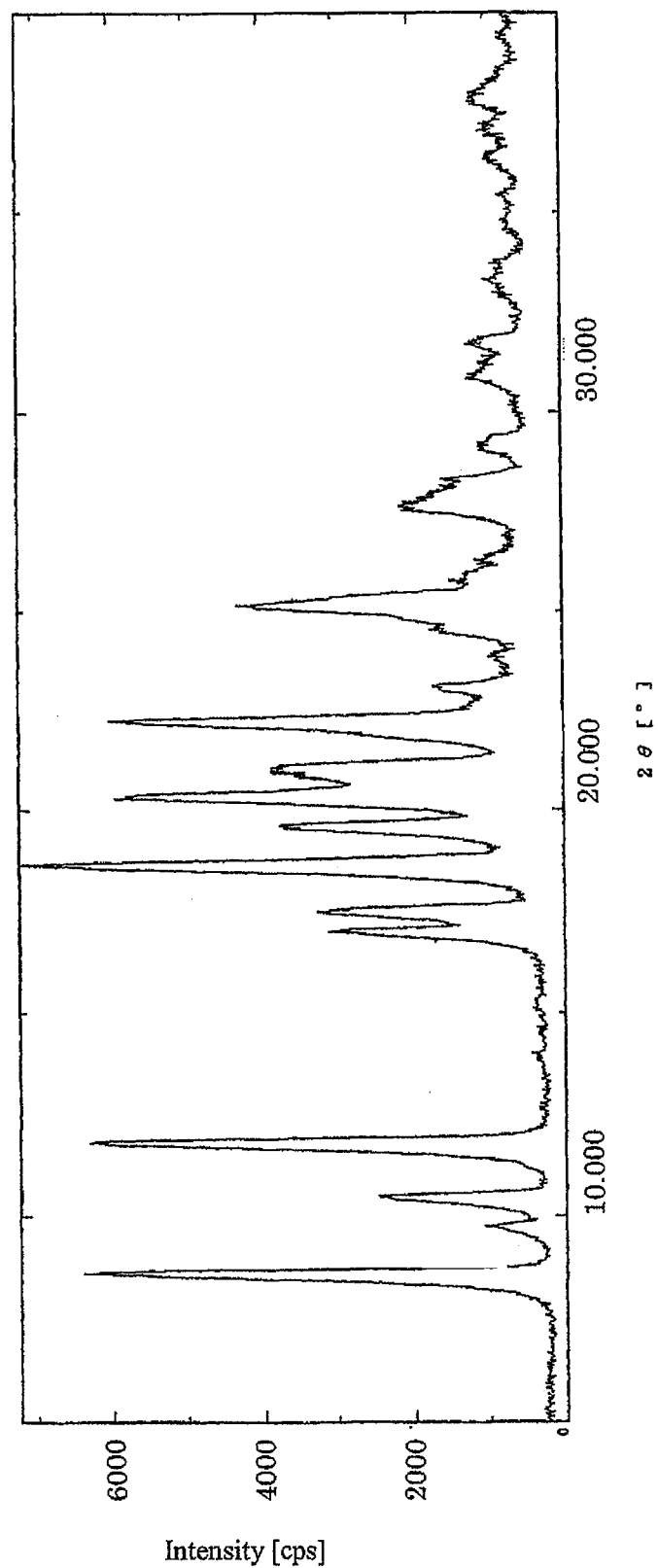

DRY POWDER PHARMACEUTICAL COMPOSITION FOR INHALATION

This application is the United States national phase application of International Application PCT/JP2009/071380 filed Dec. 24, 2009.

TECHNICAL FIELD

The present invention relates to a dry powder pharmaceutical composition for inhalation for treating or preventing influenza virus infections whose medicinal component is a compound having neuraminidase inhibitory activity and which optionally comprises a diluting agent having a specific particle size distribution. The present invention also relates to a dry powder pharmaceutical composition for inhalation for treating or preventing influenza virus infections with a specific dose and in a specific frequency of administration.

BACKGROUND ART

Japanese Patent No. 3209946 (Patent Document 1) discloses compounds having neuraminidase inhibitory activity, which include the compound represented by formula (I) shown below. The compound represented by formula (I) has excellent neuraminidase inhibitory activity and is expected to be useful as a drug for treating and preventing influenza virus infections. Japanese Patent No. 4205314 (Patent Document 2) discloses that a certain concentration of the compound represented by formula (I) can be maintained over a long time in respiratory tissues such as the lung (Patent Document 2).

The compound represented by formula (I) can produce the effect of treating/preventing influenza virus infections when administered to the respiratory system of a subject and allowed to remain in the respiratory tissues (such as the upper airway and the lung) of the subject. Therefore, the compound represented by formula (I) needs to be administered not through oral absorption but by using a dosage method and a dosage form which can deliver it to the respiratory tissues through a parenteral route.

An inhalant is a dosage form capable of being administered through a parenteral route. Examples of inhalants include a pressurized metered-dose inhalant which contains a drug dispersed in a pressurized liquefied propellant so that it can be released to atmospheric pressure and inhaled; and a dry powder inhalant. However, pressurized metered-dose inhalants, in which chlorofluorocarbon was used as a propellant, were rapidly replaced by dry powder inhalants during the 1990s, due to regulations against the use of chlorofluorocarbons and the high greenhouse effect of chlorofluorocarbon substitutes on the environment. For example, a dry powder inhalant includes zanamivir (trade name: Relenza) (Patent Document 3), which is an anti-influenza drug having neuraminidase inhibitory activity like the dry powder pharmaceutical composition of the present invention.

Specifically, dry powder inhalants consist of a powder formulation to be inhaled and a device for inhalation. The powder formulation is stored in a container such as a capsule, a blister, or a reservoir or dosing disk in a device, from which a single dose of the powder is inhaled by indrawn breath of the subject. It is reported that the size of particles capable of reaching the respiratory tissues of subjects is approximately 2 to 4 µm (Non-Patent Document 1). It is also reported that there is a correlation between the amount of a drug having a particle size of 4.7 µm or less (fine particle dose) and the amount of the drug that reaches the lung (Non-Patent Document 2). Therefore, the drugs for dry powder inhalants have to be microparticulated.

However, such a microparticulated drug has a problem in that it has a low fluidity by itself and is difficult to handle in the process of manufacturing a preparation. Such a microparticulated drug also clings to the device and may cause a problem of low sprayability.

For these problems, three improving methods have been known. One is a method of adding, to a microparticulated drug, a carrier having a particle size of 30 to 300 µm which is larger than that of the microparticulated drug so that problems with the fluidity and clinging properties of the microparticulated drug can be improved. Lactose, glucose or the like are used as the carrier. A part of the surface of particles of lactose, glucose or the like has high surface energy, and the microparticulated drug deposited on such a part is less likely to separate from the carrier. Therefore, when lactose, glucose or the like is used as the carrier, a manufacturing method (mixing-to-order method) that includes first coating the high surface energy part with fine particles and then mixing a microparticulated drug therewith is used (Non-Patent Documents 3 and 4).

Another is a method in which fine drug particles themselves or a mixture of fine drug particles and carrier particles with the same particle size are formed into loosely bound aggregates with a larger particle size.

The other is a method of forming the drug as porous particles with a high porosity based on the principle that porous particles have an aerodynamic particle size smaller than the geometric particle size. A case is reported in which porous particles show an ability to reach the lung during inhalation, which is comparable to that of fine particles, while they have a particle size at a level where a problem with fluidity or clinging is less likely to occur (Non-Patent Document 5).

No suitable dosage forms for being delivered to a recipient and delivered to the respiratory system have been found for the compound represented by the formula (I), which exhibits excellent neuraminidase inhibitory activity and is expected to be useful as a drug for treating and preventing influenza virus infections. There has been a demand for the development of a dosage method and a dosage form suitable for delivering the compound to the respiratory tissues.

Existing anti-influenza drugs, which exhibit neuraminidase inhibitory activity similarly to the compound represented by formula (I), include oseltamivir phosphate (trade name: Tamiflu, Patent Document 4) and zanamivir (trade name: Relenza, Patent Document 3). For therapy, these existing drugs have to be repeatedly administered twice daily for five days. If the number of doses can be reduced compared to that of these existing drugs, the dosing convenience can be improved. Due to its property of remaining in virus growth sites such as the lung and other organs for a long time, it is also expected to bring the advantage that, after administration once or twice, virus infection propagation can be inhibited so that secondary damage can be prevented. Thus, there has been a demand for the development of an anti-influenza drug that exhibits neuraminidase inhibitory activity at a level equal to or higher than that of the existing drugs and can be administered using a dosage amount and a dosage frequency which can provide better dosing convenience and better prevention of infection propagation than the existing drugs.

PRIOR ART DOCUMENTS

Patent Documents

[Patent Document 1] Japanese Patent Publication No. 3209946 (Specification of U.S. Pat. No. 6,340,702, Specification of European Patent No. 823428)
[Patent Document 2] Japanese Patent Publication No. 4205314
[Patent Document 3] Pamphlet of International Patent Application Laid-Open No. 91/16320
[Patent Document 4] Pamphlet of International Patent Application Laid-Open No. 96/26933

Non-Patent Documents

[Non-Patent Document 1] Thorax, 51, pp 977-980 (1996)
[Non-Patent Document 2] Interpharm Press, pp 273-281 (1996)
[Non-Patent Document 3] J. Pharm Pharmacol, 34, pp 141-145 (1982)
[Non-Patent Document 4] Powder Technol, 11, pp 41-44 (1975)
[Non-Patent Document 5] Science, 276, pp 1868 (1997)

DISCLOSURE OF THE INVENTION

Problems to be Solved by the Invention

The inventors of the present invention have been conducting earnest research for many years on drugs for treating/preventing influenza virus infections. As a result, the inventors have found that when a compound of formula (I) below having neuraminidase inhibitory activity is used as a medicinal component or when a diluting agent is added thereto and when the particle size distributions of the medicinal component and the diluting agent are controlled within specific ranges, respectively, a dry powder pharmaceutical composition for inhalation can be provided which is efficiently delivered to the respiratory tissues (such as the upper airway and lung) of a recipient (namely, has a high ability to reach the respiratory system) and which has excellent fluidity, packability, dispersibility, and inhalability. The inventors have also found good doses and a good frequency for the dry powder pharmaceutical composition of the present invention for inhalation and thus achieved the present invention.

Means for Solving the Problems

The present invention relates to the following:

[1] A dry powder pharmaceutical composition for inhalation, comprising as a medicinal component a compound represented by formula (I):

(I)

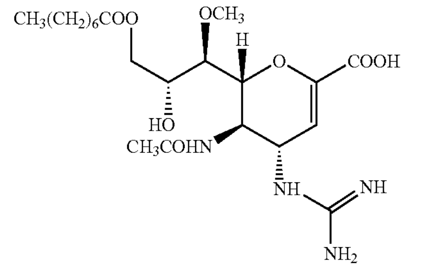

and optionally a compound represented by formula (II):

(II)

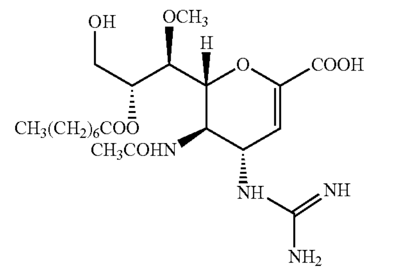

a pharmacologically acceptable salt thereof; or a hydrate thereof;

[2] The dry powder pharmaceutical composition for inhalation according to [1] above, which contains as a medicinal component a crystalline hydrate form of the compound represented by formula (I) and optionally a crystalline hydrate form of the compound represented by formula (II);

[3] The dry powder pharmaceutical composition for inhalation according to [1] above, which contains as a medicinal component a crystalline monohydrate form of the compound represented by formula (I) and optionally a crystalline monohydrate form of the compound represented by formula (II);

[4] A dry powder pharmaceutical composition for inhalation, consisting essentially of the medicinal component according to any one of [1] to [3] above;

[5] The dry powder pharmaceutical composition for inhalation according to any one of [1] to [4] above, wherein the medicinal component has a 50% by weight particle size of 3.2 μm or less and a 90% by weight particle size of 8.0 μm or less as measured by particle size analysis-laser diffraction methods;

[6] The dry powder pharmaceutical composition for inhalation according to any one of [1] to [5] above, wherein the medicinal component is prepared by a microparticulation process selected from the group consisting of a dry pulverization process (the dry pulverization process is selected from the group consisting of a jet milling process and a pin milling process), a wet pulverization process, a spray-drying process, and a freeze-drying process;

[7] The dry powder pharmaceutical composition for inhalation according to any one of [1] to [5] above, wherein the microparticulation process of the medicinal component is a jet milling process;

[8] The dry powder pharmaceutical composition for inhalation according to any one of [1], [2], [3], and [5] to [7] above, further containing a diluting agent;

[9] The dry powder pharmaceutical composition for inhalation according to [8] above, wherein the diluting agent is selected from the group consisting of a saccharide (the saccharide is selected from the group consisting of lactose, mannitol, maltose, and glucose), an amino acid (the amino acid is selected from the group consisting of phenylalanine, leucine, and glycine), a lipid (the lipid is selected from the group consisting of stearic acid, magnesium stearate, calcium stearate, sucrose fatty acid ester, sodium stearyl fumarate, and lecithin), an inorganic salt (the inorganic salt is selected from the group consisting of sodium phosphate, sodium chloride, dibasic calcium phosphate, and tribasic calcium phosphate), a lactose polymer (the lactose polymer is selected from the group consisting of polylactose and a lactic acid-glycolic acid copolymer), and hydrates thereof;

[10] The dry powder pharmaceutical composition for inhalation according to [8] above, wherein the diluting agent is lactose hydrate;

[11] The dry powder pharmaceutical composition for inhalation according to [8] above, wherein the diluting agent is a lactose hydrate or a mixture of two lactose hydrates having different particle size distributions;

[12] The dry powder pharmaceutical composition for inhalation according to [8] above, wherein the diluting agent contains:
a lactose hydrate having a particle size distribution satisfying one of
(Condition-1): the particle size distribution of the lactose hydrate measured by particle size analysis-laser diffraction methods has
a 10% by weight particle size of 5 μm to 60 μm,
a 50% by weight particle size of 50 μm to 110 μm, and
a 90% by weight particle size of 75 μm to 160 μm or
(Condition-2): in the particle size distribution measured by an air entrainment method,
the fraction with a particle size of less than 32 μm,
the fraction with a particle size of less than 63 μm, and
the fraction with a particle size of less than 100 μm
make up 5 to 10% by weight, 70 to 100% by weight, and 100% by weight, respectively; and
another lactose hydrate having a particle size distribution satisfying one of
(Condition-3): the particle size distribution of the lactose hydrate measured by particle size analysis-laser diffraction methods has
a 10% by weight particle size of 3 μm or less,
a 50% by weight particle size of 20 μm or less, and
a 90% by weight particle size of 54 μm or less or
(Condition-4): in the particle size distribution measured by an air entrainment method,
the fraction with a particle size of less than 45 μm,
the fraction with a particle size of less than 63 μm, and
the fraction with a particle size of less than 150 μm
make up 90 to 100% by weight, 98 to 100% by weight, and 100% by weight, respectively;

[13] The dry powder pharmaceutical composition for inhalation according to [12] above, wherein the diluting agent contains a lactose hydrate satisfying (Condition-1) and a lactose hydrate satisfying (Condition-3), and the lactose hydrate satisfying (Condition-1) further satisfies
(Condition-5): the particle size distribution of the lactose hydrate measured by particle size analysis-laser diffraction methods has
a 10% by weight particle size of 19 μm to 43 μm,
a 50% by weight particle size of 53 μm to 66 μm, and
a 90% by weight particle size of 75 μm to 106 μm;

[14] The dry powder pharmaceutical composition for inhalation according to [12] above, wherein the diluting agent contains a lactose hydrate satisfying (Condition-1) and the lactose hydrate satisfying (Condition-3), and a lactose hydrate satisfying (Condition-1) further satisfies
(Condition-6): the particle size distribution of the lactose hydrate measured by particle size analysis-laser diffraction methods has
a 10% by weight particle size of 5 μm to 15 μm,
a 50% by weight particle size of 50 μm to 100 μm, and
a 90% by weight particle size of 120 μm to 160 μm;

[15] The dry powder pharmaceutical composition for inhalation according to [12] above, wherein the diluting agent contains a lactose hydrate satisfying (Condition-1) and a lactose hydrate satisfying (Condition-3), and the lactose hydrate satisfying (Condition-1) further satisfies
(Condition-7): the particle size distribution of the lactose hydrate measured by particle size analysis-laser diffraction methods has
a 10% by weight particle size of 30 μm to 60 μm,
a 50% by weight particle size of 70 μm to 110 μm, and
a 90% by weight particle size of 110 μm to 150 μm;

[16] The dry powder pharmaceutical composition for inhalation according to [12] above, wherein the diluting agent contains a lactose hydrate satisfying (Condition-1) and a lactose hydrate satisfying (Condition-3), and the lactose hydrate satisfying (Condition-3) further satisfies
(Condition-8): the particle size distribution of the lactose hydrate measured by particle size analysis-laser diffraction methods has
a 10% by weight particle size of 1 μm to 3 μm,
a 50% by weight particle size of 11 μm to 20 μm, and
a 90% by weight particle size of 37 μm to 54 μm;

[17] The dry powder pharmaceutical composition for inhalation according to [12] above, wherein the diluting agent contains a lactose hydrate satisfying (Condition-1) and a lactose hydrate satisfying (Condition-3), and the lactose hydrate satisfying (Condition-3) further satisfies
(Condition-9): the particle size distribution of the lactose hydrate measured by particle size analysis-laser diffraction methods has
a 50% by weight particle size of 5 μm or less and
a 90% by weight particle size of 10 μm or less;

[18] The dry powder pharmaceutical composition for inhalation according to [12] above, wherein the diluting agent contains a lactose hydrate satisfying (Condition-2) and a lactose hydrate satisfying (Condition-3), and the lactose hydrate satisfying (Condition-3) further satisfies
(Condition-8) described in [16] above;

[19] The dry powder pharmaceutical composition for inhalation according to [12] above, wherein the diluting agent contains a lactose hydrate satisfying (Condition-2) and a lactose hydrate satisfying (Condition-4);

[20] The dry powder pharmaceutical composition for inhalation according to [12] above, wherein the diluting agent contains a lactose hydrate satisfying (Condition-1) and a lactose hydrate satisfying (Condition-4), and the lactose hydrate satisfying (Condition-1) further satisfies (Condition-5) described in [13];

[21] The dry powder pharmaceutical composition for inhalation according to [12] above, wherein the diluting agent contains a lactose hydrate satisfying (Condition-1) and a lactose hydrate satisfying (Condition-3), the lactose hydrate satisfying (Condition-1) further satisfies (Condition-5) described in [13] above, and the lactose hydrate satisfying (Condition-3) further satisfies (Condition-8) described in [16] above;

[22] The dry powder pharmaceutical composition for inhalation according to [18] above, wherein the diluting agent contains a lactose hydrate satisfying (Condition-2) and a lactose hydrate satisfying (Condition-8), and the weight ratio between the lactose hydrate satisfying (Condition-2) and the lactose hydrate satisfying (Condition-8) is from 50:50 to 100:0;

[23] The dry powder pharmaceutical composition for inhalation according to [19] above, wherein the diluting agent contains a lactose hydrate satisfying (Condition-2) and a lactose hydrate satisfying (Condition-4), and the weight ratio between the lactose hydrate satisfying (Condition-2) and the lactose hydrate satisfying (Condition-4) is from 50:50 to 100:0;

[24] The dry powder pharmaceutical composition for inhalation according to [20], wherein the diluting agent contains a lactose hydrate satisfying (Condition-5) and a lactose hydrate satisfying (Condition-4), and the weight ratio between the lactose hydrate satisfying (Condition-5) and the lactose hydrate satisfying (Condition-4) is from 50:50 to 100:0;

[25] The dry powder pharmaceutical composition for inhalation according to [21] above, wherein the diluting agent contains a lactose hydrate satisfying (Condition-5) and a lactose hydrate satisfying (Condition-8), and the weight ratio between the lactose hydrate satisfying (Condition-5) and the lactose hydrate satisfying (Condition-8) is from 50:50 to 100:0;

[26] The dry powder pharmaceutical composition for inhalation according to [18] or [22] above, wherein the diluting agent contains a lactose hydrate satisfying (Condition-2) and a lactose hydrate satisfying (Condition-8), and the lactose hydrate satisfying (Condition-2) has a particle size controlled by sieving, and the lactose hydrate satisfying (Condition-8) has a particle size controlled by pulverization;

[27] The dry powder pharmaceutical composition for inhalation according to [19] or [23] above, wherein the diluting agent contains a lactose hydrate satisfying (Condition-2) and a lactose hydrate satisfying (Condition-4), the lactose hydrate satisfying (Condition-2) has a particle size controlled by sieving, and the lactose hydrate satisfying (Condition-4) has a particle size controlled by pulverization;

[28] The dry powder pharmaceutical composition for inhalation according to [20] or [24] above, wherein the diluting agent contains a lactose hydrate satisfying (Condition-5) and a lactose hydrate satisfying (Condition-4), the lactose hydrate satisfying (Condition-5) has a particle size controlled by sieving, and the lactose hydrate satisfying (Condition-4) has a particle size controlled by pulverization;

[29] The dry powder pharmaceutical composition for inhalation according to [21] or [25] above, wherein the diluting agent contains a lactose hydrate satisfying (Condition-5) and a lactose hydrate satisfying (Condition-8), the lactose hydrate satisfying (Condition-5) has a particle size controlled by sieving, and the lactose hydrate satisfying (Condition-8) has a particle size controlled by pulverization;

[30] The dry powder pharmaceutical composition for inhalation according to any one of [1], [2], [3], and [5] to [29] above, which contains 4% by weight to 30% by weight, on an anhydrous basis, of the medicinal component;

[31] The dry powder pharmaceutical composition for inhalation according to any one of [1], [2], [3], and [5] to [29] above, which contains 15% by weight to 25% by weight, on an anhydrous basis, of the medicinal component;

[32] The dry powder pharmaceutical composition for inhalation according to any one of [1], [2], [3], and [5] to [29], which contains 20% by weight, on an anhydrous basis, of the medicinal component;

[33] The dry powder pharmaceutical composition for inhalation according to anyone of [1] to [32] above, which is manufactured by a method selected from the group consisting of a physical mixing method, a spray-drying method, and a freeze-drying method;

[34] The dry powder pharmaceutical composition for inhalation according to anyone of [1] to [32] above, which is manufactured by a physical mixing method;

[35] The dry powder pharmaceutical composition for inhalation according to any one of [1] to [34] above, which contains as a medicinal component the compound represented by formula (I) shown in [1] above and optionally the compound represented by formula (II) shown in [1] above, a pharmacologically acceptable salt thereof, or a hydrate thereof, wherein the dose of the medicinal component to be administered by inhalation to the respiratory system of a human subject before onset of an influenza virus infection is from 5 to 120 mg on an anhydrous basis;

[36] The dry powder pharmaceutical composition for inhalation according to any one of [1] to [34] above, which contains as a medicinal component the compound represented by formula (I) shown in [1] above and optionally the compound represented by formula (II) shown in [1] above, a pharmacologically acceptable salt thereof, or a hydrate thereof, wherein the dose of the medicinal component to be administered by inhalation to the respiratory system of a human subject in onset of an influenza virus infection is from 5 to 120 mg on an anhydrous basis, and the dose is to be used as a single dose or in two divided doses;

[37] The dry powder pharmaceutical composition for inhalation according to [35] or [36] above, wherein the dose of the medicinal component is 20 mg on an anhydrous basis, which is to be administered in a single inhaled dose;

[38] The dry powder pharmaceutical composition for inhalation according to [36] above, wherein the dose of the medicinal component is 20 mg on an anhydrous basis, which is to be administered in two inhaled doses;

[39] The dry powder pharmaceutical composition for inhalation according to [35] or [36] above, wherein the dose of the medicinal component is 40 mg on an anhydrous basis, which is to be administered in a single inhaled dose;

[40] The dry powder pharmaceutical composition for inhalation according to [35] or [36] above, wherein the dose of the medicinal component is 80 mg on an anhydrous basis, which is to be administered in a single inhaled dose.

The compound represented by formula (II) above (hereinafter also referred to as Compound (II) (hereinafter other compounds are also referred to similarly in the description)) can be converted into Compound (I) by an intramolecular acyl transfer reaction in which the acyloxy group in position 2 of the side chain is transferred to position 3 of the side chain. In the synthesis of Compound (I), therefore, Compound (II) can be produced together with Compound (I).

It is known that when Compound (I) is administered to warm-blooded animals, the acyloxy group in position 3 of the side chain is converted into a hydroxyl group by a metabolic reaction such as hydrolysis so that Compound (III):

(III)

[Chemical structure showing a pyran ring with OH, OCH$_3$, COOH, HO, CH$_3$COHN substituents and a guanidine group HN-C(NH)-NH$_2$]

is produced to exhibit pharmacological activity (for example see Patent Document 1). When Compound (II) is administered to warm-blooded animals, the acyloxy group in position 2 of the side chain is converted into a hydroxyl group by a metabolic reaction such as hydrolysis so that Compound (III) is also produced. In warm-blooded animals, Compound (I) and Compound (II) are both converted into the same active metabolite, Compound (III).

Therefore, both Compound (I) and Compound (II) may be medicinal components of the dry powder pharmaceutical composition of the present invention for inhalation, and a mixture of Compound (I) and Compound (II) may also be a medicinal component of the pharmaceutical composition of the present invention.

Formulae (I) and (II) described in [1] may be generically represented by formula (IV):

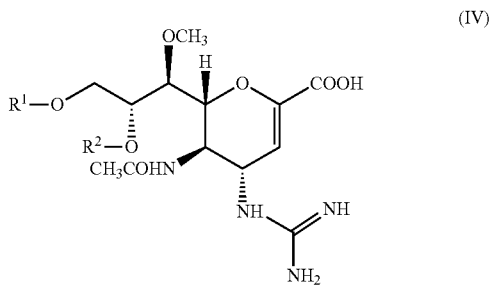

(IV)

wherein one of $R^1$ and $R^2$ represents a hydrogen atom, and the other represents a group represented by the formula $CH_3(CH_2)_6CO-$.

As described below, the present invention also encompasses a dry powder pharmaceutical composition for inhalation containing as a medicinal component a compound represented by general formula (IV'), a mixture of the compounds represented by formula general (IV'), a pharmacologically acceptable salt thereof, or a hydrate thereof. Specifically, the present invention also relates to:

(1) A dry powder pharmaceutical composition for inhalation containing as a medicinal component a compound represented by general formula (IV'):

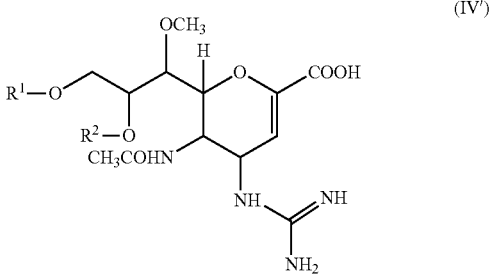

(IV')

wherein one of $R^1$ and $R^2$ represents a hydrogen atom, and the other represents a group represented by the formula $CH_3(CH_2)_6CO-$, a mixture of the compounds represented by general formula (IV'), a pharmacologically acceptable salt thereof, or a hydrate thereof;

(2) The dry powder pharmaceutical composition for inhalation according to (1) above, which contains as a medicinal component a crystalline hydrate form of the compound represented by general formula (IV') or a crystalline hydrate form of the mixture of the compound represented by general formula (IV');

(3) A dry powder pharmaceutical composition for inhalation consisting essentially of the medicinal component according to (1) or (2) above;
(4) The dry powder pharmaceutical composition for inhalation according to any one of (1) to (3) above, wherein the medicinal component has a 50% by weight particle size of 3.2 µm or less and a 90% by weight particle size of 8.0 µm or less;
(5) The dry powder pharmaceutical composition for inhalation according to any one of (1) to (4) above, wherein the medicinal component is prepared by a microparticulation process selected from the group consisting of a dry pulverization process (the dry pulverization process is selected from the group consisting of a jet milling process and a pin milling process), a wet pulverization process, a spray-drying process, and a freeze-drying process;
(6) The dry powder pharmaceutical composition for inhalation according to any one of (1) to (4) above, wherein the medicinal component is prepared by a jet milling process as a microparticulation process;
(7) The dry powder pharmaceutical composition for inhalation according to any one of (1), (2), (4), (5), and (6) above, further containing a diluting agent;
(8) The dry powder pharmaceutical composition for inhalation according to (7) above, wherein the diluting agent is selected from the group consisting of a saccharide (the saccharide is selected from the group consisting of lactose, mannitol, maltose, and glucose), an amino acid (the amino acid is selected from the group consisting of phenylalanine, leucine, and glycine), a lipid (the lipid is selected from the group consisting of stearic acid, magnesium stearate, calcium stearate, sucrose fatty acid ester, sodium stearyl fumarate, and lecithin), an inorganic salt (the inorganic salt is selected from the group consisting of sodium phosphate, sodium chloride, dibasic calcium phosphate, and tribasic calcium phosphate), a lactose polymer (the lactose polymer is selected from the group consisting of polylactose and a lactic acid-glycolic acid copolymer), and hydrates thereof;
(9) The dry powder pharmaceutical composition for inhalation according to (7) above, wherein the diluting agent is lactose hydrate;
(10) The dry powder pharmaceutical composition for inhalation according to (7) above, wherein the diluting agent is one type of lactose hydrate or a mixture of two types of lactose hydrates having different particle size distributions;
(11) The dry powder pharmaceutical composition for inhalation according to (7), wherein the diluting agent contains:
a lactose hydrate having a particle size distribution satisfying one of
(Condition-A):
the fraction with a particle size of less than 32 µm,
the fraction with a particle size of less than 63 µm, and
the fraction with a particle size of less than 100 µm
make up 5% by weight to 10% by weight, 70% by weight to 100% by weight, and 100% by weight, respectively or
(Condition-B): the lactose hydrate has
a 10% by weight particle size of 5 µm to 15 µm,
a 50% by weight particle size of 50 µm to 100 µm, and
a 90% by weight particle size of 120 µm to 160 µm; and
another lactose hydrate having a particle size distribution satisfying one of
(Condition-C):
the fraction with a particle size of less than 45 µm,
the fraction with a particle size of less than 63 µm, and
the fraction with a particle size of less than 150 µm
make up 90% by weight to 100% by weight, 98% by weight to 100% by weight, and 100% by weight, respectively or
(Condition-D): the lactose hydrate has
a 50% by weight particle size of 5 µm or less and
a 90% by weight particle size of 10 µm or less;

(12) The dry powder pharmaceutical composition for inhalation according to (11) above, wherein the diluting agent contains a lactose hydrate satisfying (Condition-A) and a lactose hydrate satisfying (Condition-C);

(13) The dry powder pharmaceutical composition for inhalation according to (11) above, wherein the diluting agent contains a lactose hydrate satisfying (Condition-A) and a lactose hydrate satisfying (Condition-C), and the weight ratio between a lactose hydrate satisfying (Condition-A) and a lactose hydrate satisfying (Condition-C) is from 75:25 to 100:0;

(14) The dry powder pharmaceutical composition for inhalation according to anyone of (11) to (13) above, wherein the diluting agent contains a lactose hydrate satisfying (Condition-A) and a lactose hydrate satisfying (Condition-C), the lactose hydrate satisfying (Condition-A) has a particle size controlled by sieving, and the lactose hydrate satisfying (Condition-C) has a particle size controlled by pulverization;

(15) The dry powder pharmaceutical composition for inhalation according to any one of (1), (2), and (4) to (14) above, which contains 4% by weight to 30% by weight of the medicinal component;

(16) The dry powder pharmaceutical composition for inhalation according to any one of (1), (2), and (4) to (14) above, which contains 15% by weight to 25% by weight of the medicinal component;

(17) The dry powder pharmaceutical composition for inhalation according to any one of (1) to (16) above, which is produced by a method selected from the group consisting of a physical mixing method, a spray-drying method, and a freeze-drying method; and

(18) The dry powder pharmaceutical composition for inhalation according to any one of (1) to (16) above, which is produced by a physical mixing method.

The 50% by weight particle size and the 90% by weight particle size of the medicinal component are determined by particle size analysis-laser diffraction methods.

The term "a mixture of the compound represented by general formula (IV')" in (1) above is intended to include a mixture of Compound (I) and Compound (II).

The present invention also provides a method of treating or preventing an influenza virus infection characterized in that the method includes administering the dry powder pharmaceutical composition of the present invention for inhalation to the respiratory system of a recipient so that a compound having neuraminidase inhibitory activity is allowed to arrive at and remain in the respiratory tissue (such as the upper airway or the lung) of the subject.

As used herein, the term "neuraminidase inhibitory activity" refers to the ability to inhibit the function of neuraminidase (the enzyme is also called sialidase), which is essential for the propagation of influenza viruses.

The medicinal component of the dry powder pharmaceutical composition of the present invention for inhalation (hereinafter also referred to as the pharmaceutical composition of the present invention) is Compound (I), namely, (2R,3R,4S)-3-acetamido-4-guanidino-2-[(1R,2R)-2-hydroxy-1-methoxy-3-(octanoyloxy)propyl]-3,4-dihydro-2H-pyran-6-carboxylic acid (it may also contain Compound (II) according to [1], namely, (2R,3R,4S)-3-acetamido-4-guanidino-2-[(1S,2R)-3-hydroxy-1-methoxy-2-(octanoyloxy)propyl]-3,4-dihydro-2H-pyran-6-carboxylic acid in addition to the compound represented by formula (I)), a pharmacologically acceptable salt thereof, or a hydrate thereof. The medicinal component is preferably a crystalline hydrate form of Compound (I) (it may further contain a crystalline hydrate form of Compound (II)), more preferably a crystalline monohydrate form of Compound (I) (it may further contain a crystalline monohydrate form of Compound (II)).

Compounds (I) and (II) each have a guanidino group and a carboxyl group in the molecule and therefore can each combine with a pharmacologically non-toxic acid or base to form a pharmacologically acceptable salt. The term "a pharmacologically acceptable salt" of Compound (I) and Compound (II) refers to such a salt.

Examples of the "pharmacologically acceptable salt" include, for example, hydrohalogenic acid salts such as hydrofluoride, hydrochloride, hydrobromide, and hydroiodide; inorganic acid salts such as nitrate, perchlorate, sulfate, and phosphate; alkanesulfonates such as methanesulfonate, ethanesulfonate, and trifluoromethanesulfonate; arylsulfonates such as benzenesulfonate and p-toluenesulfonate; organic acid salts such as acetate, trifluoroacetate, citrate, tartrate, oxalate, and maleate; amino acid salts such as glycine salt, lysine salt, arginine salt, ornithine salt, glutamic acid salt, and aspartic acid salt; alkali metal salts such as lithium salt, sodium salt, and potassium salt; alkaline earth metal salts such as calcium salt and magnesium salt; metal salts such as aluminum salt, iron salt, zinc salt, copper salt, nickel salt, and cobalt salt; organic amine salts or organic ammonium salts such as ammonium salt, tert-octylamine salt, dibenzylamine salt, morpholine salt, glucosamine salt, ethylenediamine salt, guanidine salt, diethylamine salt, triethylamine salt, dicyclohexylamine salt, procaine salt, ethanolamine salt, diethanolamine salt, piperazine salt, and tetramethylammonium salt. Preferably, the pharmacologically acceptable salt is an alkali metal salt such as a lithium salt, a sodium salt or a potassium salt; an organic acid salt such as an acetate or a trifluoroacetate; or an inorganic acid salt such as a hydrochloride or a sulfate.

In some cases, Compound (I), Compound (II), and pharmacologically acceptable salts thereof each absorb water to form a hydrate when allowed to stand in the air or mixed with water. A hydrate of Compound (I), Compound (II), or a pharmacologically acceptable salt thereof is intended to include such a hydrate.

A crystalline hydrate form of Compound (I): (2R,3R,4S)-3-acetamido-4-guanidino-2-[(1R,2R)-2-hydroxy-1-methoxy-3-(octanoyloxy)propyl]-3,4-dihydro-2H-pyran-6-carboxylic acid is disclosed in Japanese Patent Publication No. 3920041 (corresponding to U.S. Pat. No. 6,844,363 or European Patent Publication No. 1277750), which shows main peaks at interplanar spacings of 4.0, 4.4, 4.7, 7.5, and 10.2 angstroms in an X-ray powder diffraction obtained with copper Kα line radiation.

As used herein, the term "main peaks" refers to peaks that have a relative intensity of 80 or more when the intensity of the peak at an interplanar spacing d of 4.7 angstroms is normalized as 100.

The interplanar spacing (in units of angstroms) may be calculated from the formula $2d \sin \theta = n\lambda$, wherein $n=1$.

The particle size distribution of the medicinal component of the pharmaceutical composition of the present invention preferably has a 50% by weight particle size D50 of 3.2 μm or less as measured by particle size analysis-laser diffraction methods and also preferably has a 90% by weight particle size D90 of 8.0 μm or less as measured by particle size analysis-laser diffraction methods. In these ranges, the medicinal component according to the present invention has particularly excellent inhalability and a high ability to reach the respiratory system and therefore can reach deep portions of the lung through the pharynx, so that it can exhibit high and long-term anti-influenza activity.

The pharmaceutical composition of the present invention may consist essentially of the medicinal component or may contain a diluting agent in addition to the medicinal component.

When mixed with the medicinal component, the diluting agent serves as a carrier to carry the medicinal component on its surface and to deliver the medicinal component. When the diluting agent is mixed with the medicinal component, the pharmaceutical composition of the present invention can be prevented from aggregation.

The diluting agent may be selected from the group consisting of a saccharide (the saccharide is selected from the group consisting of lactose, mannitol, maltose, and glucose), an amino acid (the amino acid is selected from the group consisting of phenylalanine, leucine, and glycine), a lipid (the lipid is selected from the group consisting of stearic acid, magnesium stearate, calcium stearate, sucrose fatty acid ester, sodium stearyl fumarate, and lecithin), an inorganic salt (the inorganic salt is selected from the group consisting of sodium phosphate, sodium chloride, dibasic calcium phosphate, and tribasic calcium phosphate), a lactose polymer (the lactose polymer is selected from the group consisting of polylactose and a lactic acid-glycolic acid copolymer), and hydrates thereof.

In particular, the diluting agent is preferably a saccharide, more preferably lactose, even more preferably lactose hydrate. In general, lactose hydrate is in the form of a crystal.

The Japanese Pharmacopoeia Fifteenth Edition defines lactose hydrate as the "monohydrate of β-D-galactopyranosyl-(1→4)-α-glucopyranose", which is also called α-lactose hydrate. Therefore, the terms "lactose hydrate" and "α-lactose hydrate" are synonymous.

A single diluting agent or a mixture of two or more diluting agents may be used. A mixture of two or more powders of a single kind of diluting agent, which have two or more different particle size distributions from each other may also be used.

In particular, a mixture of two lactose hydrates having different particle size distributions is preferably used. When a mixture of two or more diluting agents having different particle size distributions are used, the medicinal component deposited on the diluting agent surface can be easily dispersed upon discharge from an inhaler by the recipient's inspiration, which is preferred.

Two lactose hydrates having different particle size distributions preferably include a lactose hydrate having a particle size distribution satisfying one of (Condition-1) or (Condition-2) shown below and another lactose hydrate having a particle size distribution satisfying one of (Condition-3) or (Condition-4) shown below.

(Condition-1): The particle size distribution of the lactose hydrate measured by particle size analysis-laser diffraction methods has
a 10% by weight particle size of 5 μm to 60 μm,
a 50% by weight particle size of 50 μm to 110 μm, and
a 90% by weight particle size of 75 μm to 160 μm.

(Condition-2): In the particle size distribution measured by an air entrainment method,
the fraction with a particle size of less than 32 μm,
the fraction with a particle size of less than 63 μm, and
the fraction with a particle size of less than 100 μm
make up 5 to 10% by weight, 70 to 100% by weight, and 100% by weight, respectively.

(Condition-3): The particle size distribution of the lactose hydrate measured by particle size analysis-laser diffraction methods has
a 10% by weight particle size of 3 μm or less,
a 50% by weight particle size of 20 μm or less, and
a 90% by weight particle size of 54 μm or less.

(Condition-4): In the particle size distribution measured by an air entrainment method,
the fraction with a particle size of less than 45 μm,
the fraction with a particle size of less than 63 μm, and
the fraction with a particle size of less than 150 μm
make up 90 to 100% by weight, 98 to 100% by weight, and 100% by weight, respectively.

The particle size analysis-laser diffraction methods include applying laser light to a group of particles to determine the distribution pattern of the intensity of diffracted light/scattered light produced therefrom and calculating the particle size distribution from the distribution pattern of the intensity. The measurement methods are internationally standardized and described in ISO 13320 issued by International Organization for Standardization. The 10% by weight particle size, the 50% by weight particle size, and the 90% by weight particle size are defined as particle sizes at 10%, 50%, and 90%, respectively, in the weight cumulative particle size distribution curve obtained by the particle size analysis-laser diffraction methods.

The air entrainment method includes determining the particle size distribution with sieves while sprinkling the powder with a standardized air jet. The air entrainment method is described in the Japanese Pharmacopoeia, "General Tests, 3. Method of measurement of physical properties of powders, 3.04 Particle size determination, Method 2 Analytical sieving, (2) Air entrainment methods, air jet" (see The Japanese Pharmacopoeia Fifteenth Edition, Hirokawa Publishing Company, page 158). Concerning the sieves used for the measurement, the Japanese Pharmacopoeia Fifteenth Edition, "Table 3.04-1, Size of standard sieve series in range of interest" (page 154) describes Japanese Pharmacopoeial sieve numbers and the corresponding ISO nominal sieve numbers, USP sieve numbers, and EP sieve numbers. Therefore, the measurement method can apply to the United States or European particle size distribution test. Specifically, for example, the measurement may be performed by the air entrainment method using Alpine Air Jet Sieve, a powder particle size analyzer developed by ALPINE (Germany), as described in the Japanese Pharmacopoeia Fifteenth Edition (Hirokawa Publishing Company, 2006), "B. General Tests, 3.04 Particle size determination, Method 2 Analytical sieving, Sieving methods, 2) Air entrainment methods, air jet and sonic shifter sieving" (page B-421), Note 20. The measurement result is obtained as a weight percentage (%) of the powder in the sieve size range after the weight of the sample remaining on the sieve is precisely measured. For example, when the sieve size is d μm and when the proportion of the weight of the powder passing through the sieve is A % by weight, the amount of the fraction with a particle size of less than d μm is A % by weight.

Preferred examples of the particle size distribution satisfying (Condition-1) include (Condition-5), (Condition-6), and (Condition-7) described below.

(Condition-5): The particle size distribution of the lactose hydrate measured by particle size analysis-laser diffraction methods has
a 10% by weight particle size of 19 to 43 μm,
a 50% by weight particle size of 53 to 66 μm, and
a 90% by weight particle size of 75 to 106 μm.

(Condition-6): The particle size distribution of the lactose hydrate measured by particle size analysis-laser diffraction methods has
a 10% by weight particle size of 5 to 15 μm,
a 50% by weight particle size of 50 to 100 μm, and
a 90% by weight particle size of 120 to 160 μm.

(Condition-7): The particle size distribution of the lactose hydrate measured by particle size analysis-laser diffraction methods has
a 10% by weight particle size of 30 to 60 μm,
a 50% by weight particle size of 70 to 110 μm, and
a 90% by weight particle size of 110 to 150 μm.

Preferred examples of the particle size distribution satisfying (Condition-3) include (Condition-8) and (Condition-9) described below.

(Condition-8): The particle size distribution of the lactose hydrate measured by particle size analysis-laser diffraction methods has
a 10% by weight particle size of 1 to 3 μm,
a 50% by weight particle size of 11 to 20 μm, and
a 90% by weight particle size of 37 to 54 μm.

(Condition-9): The particle size distribution of the lactose hydrate measured by particle size analysis-laser diffraction methods has
a 50% by weight particle size of 5 μm or less and
a 90% by weight particle size of 10 μm or less.

A combination of two lactose hydrates having different particle size distributions is preferably a combination of a lactose hydrate satisfying (Condition-1) and another lactose hydrate satisfying (Condition-3), more preferably a combination of a lactose hydrate satisfying (Condition-1) and another lactose hydrate satisfying (Condition-4), even more preferably a combination of a lactose hydrate satisfying (Condition-2) and another lactose hydrate satisfying (Condition-3), in particular, preferably a combination of a lactose hydrate satisfying (Condition-2) and another lactose hydrate satisfying (Condition-4).

Preferred examples of a combination of a lactose hydrate satisfying (Condition-2) and another lactose hydrate satisfying (Condition-3) include a combination of a lactose hydrate satisfying (Condition-2) and another lactose hydrate satisfying (Condition-8) and a combination of a lactose hydrate satisfying (Condition-2) and another lactose hydrate satisfying (Condition-9).

Preferred examples of a combination of a lactose hydrate satisfying (Condition-1) and another lactose hydrate satisfying (Condition-4) include a combination of a lactose hydrate satisfying (Condition-5) and another lactose hydrate satisfying (Condition-4), a combination of a lactose hydrate satisfying (Condition-6) and another lactose hydrate satisfying (Condition-4), and a combination of a lactose hydrate satisfying (Condition-7) and another lactose hydrate satisfying (Condition-4).

Preferred examples of a combination of a lactose hydrate satisfying (Condition-1) and another lactose hydrate satisfying (Condition-3) include a combination of a lactose hydrate satisfying (Condition-5) and another lactose hydrate satisfying (Condition-3), a combination of a lactose hydrate satisfying (Condition-6) and another lactose hydrate satisfying (Condition-3), a combination of a lactose hydrate satisfying (Condition-7) and another lactose hydrate satisfying (Condition-3), a combination of a lactose hydrate satisfying (Condition-1) and another lactose hydrate satisfying (Condition-8), and a combination of a lactose hydrate satisfying (Condition-1) and another lactose hydrate satisfying (Condition-9).

Among these combinations, particularly preferred are a combination of a lactose hydrate satisfying (Condition-2) and another lactose hydrate satisfying (Condition-8), a combination of a lactose hydrate satisfying (Condition-2) and another lactose hydrate satisfying (Condition-4), a combination of a lactose hydrate satisfying (Condition-5) and another lactose hydrate satisfying (Condition-4), and a combination of a lactose hydrate satisfying (Condition-5) and another lactose hydrate satisfying (Condition-8).

When the diluting agent has a particle size distribution in such a range, the pharmaceutical composition of the present invention resists gathering or clinging in an inhaler and has good fluidity and good sprayability from an inhaler, which is preferred. In addition, the medicinal component deposited on the diluting agent surface can easily be separated from the diluting agent in the air flow produced by the recipient's inspiration, so that it can efficiently reach the respiratory tissues of the recipient, which is also preferred.

The diluting agent preferably comprises a lactose hydrate satisfying (Condition-1) and another lactose hydrate satisfying (Condition-3), wherein the weight ratio between the lactose hydrate satisfying (Condition-1) and the lactose hydrate satisfying (Condition-3) is preferably from 50:50 to 100:0, more preferably from 75:25 to 100:0.

More preferably, the diluting agent comprises a lactose hydrate satisfying (Condition-2) and another lactose hydrate satisfying (Condition-8), wherein the weight ratio between the lactose hydrate satisfying (Condition-2) and the lactose hydrate satisfying (Condition-8) is from 50:50 to 100:0; a lactose hydrate satisfying (Condition-2) and another lactose hydrate satisfying (Condition-4), wherein the weight ratio between the lactose hydrate satisfying (Condition-2) and the lactose hydrate satisfying (Condition-4) is from 50:50 to 100:0; a lactose hydrate satisfying (Condition-5) and another lactose hydrate satisfying (Condition-4), wherein the weight ratio between the lactose hydrate satisfying (Condition-5) and the lactose hydrate satisfying (Condition-4) is from 50:50 to 100:0; or a lactose hydrate satisfying (Condition-5) and another lactose hydrate satisfying (Condition-8), wherein the weight ratio between the lactose hydrate satisfying (Condition-5) and the lactose hydrate satisfying (Condition-8) is from 50:50 to 100:0.

When the diluting agent has a content ratio in such a range, the pharmaceutical composition of the present invention has good fluidity, so that it can be easily charged into capsules or inhalers, which is preferred. It also has a high ability to be inhaled by the recipient.

The pharmaceutical composition of the present invention preferably contains 4% by weight to 30% by weight, on an anhydrous basis, of the medicinal component, more preferably 15% by weight to 25% by weight, on an anhydrous basis, of the medicinal component. In such a range, the pharmaceutical composition of the present invention has good fluidity, makes it possible to form a uniform mixture of the medicinal component and the diluting agent, and can be loaded into an inhaler with high precision. In such a range, the pharmaceutical composition of the present invention also has good fluidity in an inhaler, allows easy separation of the medicinal component from the diluting agent upon discharge from the inhaler, and makes it possible to deliver a relatively high proportion of the medicinal component to the respiratory tissues.

The pharmaceutical composition of the present invention is taken into the respiratory tissues of the recipient by the recipient's inspiration. The respiratory system include the upper airway including the oropharynx and larynx, the trachea, the bronchia, the bronchiole, the respiratory bronchioles, and the lower airway to deep portions of the lung. The dry powder pharmaceutical composition of the present invention for inhalation is taken into the respiratory system of the recipient by the inhalation and deposited on the epithelium of the upper airway and the lower airway, where the medicinal component is hydrolyzed and absorbed into the cells to exhibit anti-influenza activity by inhibiting the viral growth.

The pharmaceutical composition of the present invention may be packaged for administration of a specific dose. Examples of such a package include a capsule such as a hard gelatin capsule or a hydroxypropylmethylcellulose (HPMC) capsule, a cartridge, and a blister package. A specific amount of the pharmaceutical composition of the present invention may also be directly loaded into an inhaler for administration. The pharmaceutical composition of the present invention is in the form of a dry powder. Therefore, an inhaler generally belonging to a dry powder inhaler (DPI) may be used.

The pharmaceutical composition of the present invention is useful as a drug for treating or preventing type A or type B influenza infection.

The dose of the therapeutic or prophylactic agent of the present invention depends on the type of the medicinal component to be used, the degree of influenza prevalence, and conditions such as the body weight or age of the patient to be administered. Preferably, the therapeutic or prophylactic agent of the present invention is administered to a human subject by inhalation in a dose of 10 μg to 5 mg per 1 kg body weight once to seven times a week or once to three times a day.

It is particularly preferable to administer the pharmaceutical composition of the present invention, which comprises 5 to 120 mg, on an anhydrous basis, of Compound (I) (and optionally Compound (II)), a pharmacologically acceptable salt thereof, or a hydrate thereof as a dose of medicinal component, and comprises the diluting agent (preferably lactose hydrates with the particle sizes controlled as described above) for the prevention of an influenza virus infection by inhalation to the respiratory system of a human subject before onset of the influenza virus infection and for the treatment of an influenza virus infection in a single dose or two divided doses by inhalation to the respiratory system of a human subject in onset of the influenza virus infection.

When the pharmaceutical composition of the present invention is administered as a prophylactic agent, it may be administered intermittently to the respiratory system of a human subject before onset of an influenza virus infection. Each administration may be performed one at a time. For example, the interval between administrations is 5 to 10 days or a week.

In actual medical situations, prophylactic administration may be performed regardless of the presence or absence of influenza virus infection before onset of influenza symptoms. The time when the prophylactic agent of the present invention is administered is also intended to include the time when the administration is performed regardless of the presence or absence of the infection before onset of symptoms.

When the pharmaceutical composition of the present invention is administered as a therapeutic agent, it may be administered in a single dose or in two divided doses by inhalation to the respiratory tissues of a human subject after onset of an influenza virus infection.

As used herein, the term "before onset" means the state in which no influenza symptom appears regardless of the presence or absence of virus infection.

As used herein, the term "in onset" means that as a result of influenza virus infection, subjective symptoms such as fever appear.

Influenza symptoms are intended to include headache, malaise, myalgia (or arthralgia), chill, fever, perspiration, pituita, sore throat, cough, sneeze, and the like.

The medicinal component of the agent for preventing an influenza virus infection is more preferably administered in a single inhaled dose of 20 mg on an anhydrous basis; in a single inhaled dose of 40 mg on an anhydrous basis; or in a single inhaled dose of 80 mg on an anhydrous basis. Most preferably, the medicinal component is administered in a single inhaled dose of 40 mg on an anhydrous basis.

The medicinal component of the agent for treating an influenza virus infection is more preferably administered in a single inhaled dose of 20 mg on an anhydrous basis; in a single inhaled dose of 40 mg on an anhydrous basis; in two divided doses of 40 mg (namely in two doses of 20 mg each); or in a single inhaled dose of 80 mg on an anhydrous basis. Most preferably, the medicinal component of the therapeutic agent is administered in a single inhaled dose of 40 mg on an anhydrous basis.

The recipient is preferably an animal such as a mammal, more preferably a human or any member of the genus *Equus*, such as horse, donkey, or mule. The subject is most preferably a human.

Effects of the Invention

The pharmaceutical composition of the present invention has good fluidity and therefore can be loaded into an inhaler easily and precisely. The pharmaceutical composition of the present invention has high dispersibility and can be easily inhaled even by a recipient with weak inhalation capabilities as well as by a recipient with normal or strong inhalation capabilities.

The pharmaceutical composition of the present invention having the specified particle size distribution can reach the respiratory system of the recipient, in particular, to the upper airway or the lung, and therefore is effective in providing high and long-term anti-influenza activity.

The pharmaceutical composition of the present invention inhibits viral growth when administered in a specific dose only a small number of times, such as once or twice, and is highly effective in treating/preventing influenza.

BRIEF DESCRIPTION OF THE DRAWING

FIG. 1 is an X-ray powder diffraction pattern obtained with copper Kα line radiation (wavelength λ=1.54 angstroms) for a crystalline form of (2R,3R,4S)-3-acetamido-4-guanidino-2-[(1R,2R)-2-hydroxy-1-methoxy-3-(octanoyloxy)propyl]-3,4-dihydro-2H-pyran-6-carboxylic acid hydrate obtained in Production Example 1.

The vertical axis of the X-ray powder diffraction pattern represents diffraction intensity in units of counts/second (cps), and the horizontal axis represents diffraction angle 2θ (degrees).

The interplanar spacing d (angstroms) may be calculated from the formula $2d \sin \theta = n\lambda$, wherein n=1.

BEST MODES FOR CARRYING OUT THE INVENTION

Compound (I), Compound (II), or a pharmacologically acceptable salt thereof may be produced according to or based on the method disclosed in Japanese Patent No. 3209946 (Patent Document 1).

A crystalline form of Compound (I), a crystalline form of Compound (II), or a crystalline hydrate form thereof may be produced according to or based on the method disclosed in Japanese Patent Application Laid-Open (JP-A) No. 2002-012590 (Japanese Patent Publication No. 3920041, Specification of U.S. Pat. No. 6,844,363, or Specification of European Patent No. 1277750).

The medicinal component of the pharmaceutical composition of the present invention preferably has a 50% by weight particle size of 3.2 μm or less and a 90% by weight particle size of 8.0 μm or less as measured by particle size analysis-laser diffraction methods.

The process used to microparticulate the medicinal component of the pharmaceutical composition of the present invention is preferably, but not limited to, a process selected from the group consisting of a dry pulverization process, a wet pulverization process, a spray-drying process, and a freeze-drying process.

The means for microparticulation by the dry pulverization process are not particularly limited, but preferably a jet grinding process such as a jet milling process, an impact grinding process such as a pin milling process or a hammer milling process, or a grinding process such as a pulverizer process, more preferably a jet milling process.

The means for microparticulation by the wet pulverization process are not particularly limited, but, for example, a bead milling process, a ball milling process, or an ultra-high pressure jet process can be employed.

The bead milling process includes adding a slurry of the object compound dispersed in a solvent to a vessel containing beads of glass, zirconia, alumina, or the like and allowing the particles to pass through the vessel while agitating the slurry with a rotary blade so that microparticulation is achieved by the impact force during the collision with the beads and by the shearing force during passing between the beads. In general, it can reduce the particle size to the smallest level among the dry and wet pulverization processes.

The ball milling process uses the same process as the dry bead milling process, except that a dispersion of particles in a solvent is used as the object to be pulverized.

The bead milling process and the ball milling process both use colliding media other than the particles. Such media used in bead milling process, may be zirconia, alumina, glass, or metal powder with a particle size of about 1 μm to about 1 mm, and such media used in the ball milling process may be zirconia, alumina, nylon, or metal balls with a particle size of about 1 mm to several cm.

The ultra-high pressure jet process includes allowing accelerated particles to collide against one another to microparticulate them.

The spray-drying process includes spraying fine droplets of a solution of the object compound and applying a hot wind to them to evaporate the solvent in a short time so that dry fine particles are formed. For example, the spray dryer used may be a rotating disc type, pressure nozzle type, two-fluid nozzle type, pressure two-fluid nozzle type, or four-fluid nozzle type spray dryer, depending on the droplet-producing method. Means for microparticulation by the spray-drying process is not restricted and may be any of the above spray dryers. The spray dryer is preferably of a two-fluid nozzle type, a pressure two-fluid nozzle type, or a four-fluid nozzle type.

The freeze-drying process includes quickly cooling a solution of the object compound to a low temperature to quickly freeze it and then sublimating water under reduced pressure to form dry fine particles. Freeze drying may be further performed, and then air impact may be applied so that microparticulation can be achieved.

The process of microparticulating the medicinal component of the pharmaceutical composition of the present invention is preferably the dry pulverization process, more preferably the jet milling process. The jet milling process is preferred, because fine particles being produced by the jet milling process are less clinging and have excellent handleability.

The process of controlling the particle size of the diluting agent in the pharmaceutical composition of the present invention is preferably, but not limited to, a microparticulation process selected from the group consisting of a dry pulverization process, a wet pulverization process, a spray-drying process, and a freeze-drying process, a classification process selected from the group consisting of a sieve classification process and an airflow classification process, or a combination of the microparticulation process and the classification process.

The process of controlling the particle size of the lactose hydrate satisfying one of (Condition-1) and (Condition-2) shown below is preferably the classification process. The process of controlling the particle size of the lactose hydrate satisfying one of (Condition-3) and (Condition-4) shown below is preferably the microparticulation process such as the dry pulverization process.

(Condition-1): The particle size distribution of the lactose hydrate measured by particle size analysis-laser diffraction methods has
a 10% by weight particle size of 5 μm to 60 μm,
a 50% by weight particle size of 50 μm to 110 μm, and
a 90% by weight particle size of 75 μm to 160 μm.
(Condition-2): In the particle size distribution measured by an air entrainment method,
the fraction with a particle size of less than 32 μm,
the fraction with a particle size of less than 63 μm, and
the fraction with a particle size of less than 100 μm
make up 5 to 10% by weight, 70 to 100% by weight, and 100% by weight, respectively.
(Condition-3): The particle size distribution of the lactose hydrate measured by particle size analysis-laser diffraction methods has
a 10% by weight particle size of 3 μm or less,
a 50% by weight particle size of 20 μm or less, and
a 90% by weight particle size of 54 μm or less.
(Condition-4): In the particle size distribution measured by an air entrainment method,
the fraction with a particle size of less than 45 μm,
the fraction with a particle size of less than 63 μm, and
the fraction with a particle size of less than 150 μm
make up 90 to 100% by weight, 98 to 100% by weight, and 100% by weight, respectively.

Methods of manufacturing a dry powder for inhalation are broadly classified into a method of mixing a medicinal component whose particle size has been previously controlled with a diluting agent whose particle size has been previously controlled; and a method including mixing a medicinal component and a diluting agent and then microparticulating the mixture.

In the former method, a medicinal component whose particle size is controlled by a dry pulverization process, a wet pulverization process, a spray-drying process, or a freeze-drying process and a diluting agent whose particle size is controlled by a microparticulation process selected from the group consisting of a dry pulverization process, a wet pulverization process, a spray-drying process, and a freeze-drying process, a classification process selected from the group consisting of a sieve classification process and an airflow classification process, or a combination of the microparticulation process and the classification process are first separately produced. Subsequently, the medicinal component whose particle size has been controlled is granulated alone, or the medicinal component whose particle size has been controlled and the diluting agent whose particle size has been controlled are mixed in a specific ratio and granulated, so that a pharmaceutical composition is formed. For example, the spray-drying process may be based on the process described in the specification of U.S. Patent Application Publication No. 2008/0063722. For example, the freeze-drying process may be based on the process described in the pamphlet of International Patent Application Publication No. 2002/102445.

Examples of the method of granulating the medicinal component alone include fluidized bed granulation and spray drying.

Examples of the method of mixing and granulating the medicinal component and the diluting agent include a physical mixing method using a sieving machine such as a granulator and hand sieving, a rotary vessel mixer such as a V-type mixer, a W-type mixer, a Bohle mixer, and a tumbling mixer, and a rotary blade mixer such as a ribbon blender or a Henschel mixer; a spray-drying method including spray-drying a solution or dispersion of the medicinal component and the diluting agent in an appropriate solvent; a mechano-fusion method including forming composite particles of the medicinal component and the diluting agent by a mechano-chemical reaction; and a fluidized bed granulation method.

In the latter method, the medicinal component and the diluting agent are mixed in a predetermined ratio, and then microparticulation and particle size control are simultaneously performed by a microparticulation process selected from the group consisting of a dry pulverization process, a wet pulverization process, a spray-drying process, and a freeze-drying process. When the type of the diluting agent, the microparticulation process, and the conditions for the process are appropriately selected, particles with a high porosity can be obtained, and the property of reaching larynx, upper trachea, bronchia, and deep portions of the lung during oral inhalation similarly to fine particles can be imparted to particles, while they are prevented from gathering or clinging and allowed to have a particle size distribution capable of providing excellent fluidity and handleability.

Among the above production methods, the method of producing the pharmaceutical composition of the present invention is preferably selected from the group consisting of the physical mixing method, the spray-drying method and the freeze-drying method, more preferably the physical mixing method.

The diluting agent for use in the former method, which includes mixing the medicinal component whose particle size has been previously controlled with the diluting agent whose particle size has been previously controlled, may comprise a lactose hydrate satisfying one of (Condition-1) or (Condition-2) described above and another lactose hydrate satisfying one of (Condition-3) or (Condition-4) described above. In this case, the lactose hydrates are preferably mixed first, and then the medicinal component whose particle size has been controlled is preferably added thereto and mixed. When the mixing processes are performed in this order, the medicinal component deposited on the diluting agent surface can easily separate from the diluting agent in the air flow produced by the recipient's inspiration, so that it can more efficiently reach the respiratory system of the recipient, which is preferred.

The pharmaceutical composition of the present invention is preferably produced in an environment with controlled temperature and humidity.

The optimum temperature range and the optimum humidity range depend on the production method, the machine, and the type of the diluting agent to be used. For example, when the medicinal component microparticulated by the spray-drying process and the diluting agent whose particle size is controlled are mixed by the physical mixing method, the temperature is preferably controlled in the range of 19° C. to 27° C., and the relative humidity is preferably controlled in the range of 30% RH to 65% RH.

EXAMPLES

Hereinafter, some examples, preparation examples, and test examples are shown to describe the present invention more specifically.

Production Example 1

Crystalline monohydrate form of (2R,3R,4S)-3-acetamido-4-guanidino-2-[(1R,2R)-2-hydroxy-1-methoxy-3-(octanoyloxy)propyl]-3,4-dihydro-2H-pyran-6-carboxylic acid [Compound (I)]

Diphenylmethyl 5-acetamido-4-(N,N'-bis-t-butyloxycarbonyl)guanidino-9-O-octanoyl-2,3,4,5-tetradeoxy-7-O-methyl-D-glycero-D-galacto-non-2-enopyranosoate (3.46 g, 4.1 mmol), which is the compound disclosed in Example 35(i) of Japanese Patent Publication No. 3209946 (Patent Document 1), was dissolved in a mixture of methylene chloride (27 ml) and trifluoroacetic acid (14 ml), and the resulting solution was stirred at room temperature overnight.

After the reaction mixture was concentrated to dryness under reduced pressure, the residue was azeotropically concentrated to dryness three times with toluene (5 ml).

The resulting oily product was dissolved in ethyl acetate (10 ml).

The solution was poured into a saturated aqueous sodium hydrogen carbonate solution (50 ml), and a 20% aqueous sodium carbonate solution was added to adjust the pH to 8.5.

After the solution was stirred at room temperature for 3 hours, the pH of the solution was adjusted to 5.0 with hydrochloric acid (3 ml), and the solution was stirred at room temperature for 1 hour.

After the solution was further stirred under ice cooling for 1 hour, the resulting crystals were separated by suction filtration and dried under vacuum at an external temperature of 50° C. for 10 hours.

The crystals were allowed to stand in the air for a day, so that the title target compound was obtained in a crystalline form (0.97 g, 51% yield).

The resulting crystalline form contained Compound (II) [(2R,3R,4S)-3-acetamido-4-guanidino-2-[(1S,2R)-3-hydroxy-1-methoxy-2-(octanoyloxy)propyl]-3,4-dihydro-2H-pyran-6-carboxylic acid monohydrate] in addition to the title target compound (I).

IR spectrum (KBr) vmax cm$^{-1}$: 3412, 2929, 2856, 1676, 1401, 1320, 1285, 1205, 1137, 722.

$^1$H NMR spectrum (400 MHz, CD$_3$OD) δppm: 5.88 (1H, d, J=2.5 Hz), 4.45 (3H, m), 4.27 (1H, dd, J=10.0 Hz, 10.0 Hz), 4.15 (1H, m), 3.47 (2H, m), 3.42 (3H, s), 2.37 (2H, t, J=7.4 Hz), 2.10 (3H, s), 1.31 (2H, m), 1.20-1.40 (8H, m), 0.85-0.95 (3H, m).

$^{13}$CNMR spectrum (100 MHz, CD$_3$OD) δppm: 176.5, 173.7, 164.7, 158.9, 146.7, 108.7, 80.1, 78.0, 69.3, 66.8, 61.4, 52.4, 35.1, 32.8, 30.2, 30.1, 26.0, 23.7, 22.8, 14.4.

FIG. 1 shows an X-ray powder diffraction pattern obtained with copper Kα line radiation (wavelength λ=1.54 angstroms) for the resulting crystalline product. The vertical axis of the X-ray powder diffraction pattern represents diffraction intensity in units of counts/second (cps), and the horizontal axis represents diffraction angle 2θ (degrees).

Table 1 shows the particle size distributions of lactose hydrates used in the examples below. As shown in Table 1, the lactose hydrates used in the examples below are named Lactose 1 to Lactose 7, respectively.

TABLE 1

| Lactose | (trade name) | Particle size distribution |
|---|---|---|
| Lactose 1 | Respitose SV003 (DMV-Fonterra Excipients) | Fraction with particle size less than 32 μm: 5 to 10 wt % Fraction with particle size less than 63 μm: 70 to 100 wt % Fraction with particle size less than 100 μm: 100 wt % (measured by air entrainment method) |
| Lactose 2 | Respitose ML006 (DMV-Fonterra Excipients) | Fraction with particle size less than 45 μm: 90 to 100 wt % Fraction with particle size less than 63 μm: 98 to 100 wt % Fraction with particle size less than 150 μm: 100 wt % (measured by air entrainment method) |
| Lactose 3 | Respitose ML001 (DMV-Fonterra Excipients) | Fraction with particle size less than 45 μm: 40 to 60 wt % Fraction with particle size less than 100 μm: 75 to 100 wt % Fraction with particle size less than 150 μm: 90 to 100 wt % Fraction with particle size less than 315 μm: 90.5 to 100 wt % (measured by air entrainment method) |
| Lactose 4 | Respitose ML003 (DMV-Fonterra Excipients) | Fraction with particle size less than 45 μm: 50 to 65 wt % Fraction with particle size less than 100 μm: 90 to 100 wt % Fraction with particle size less than 150 μm: 96 to 100 wt % (measured by air entrainment method) |
| Lactose 5 | Pharmatose 80 (DMV-Fonterra Excipients) | 10 wt % particle size: 20 to 120 μm 50 wt % particle size: 130 to 230 μm 90 wt % particle size: 235 to 295 μm (measured by particle size analysis-laser diffraction methods) |
| Lactose 6 | Lactohale LH200 (Friesland Foods Domo) | 10 wt % particle size: 5 to 15 μm 50 wt % particle size: 50 to 100 μm 90 wt % particle size: 120 to 160 μm (measured by particle size analysis-laser diffraction methods) |
| Lactose 7 | InhaLac 230 (Molkerei Meggle Wasserburg GmbH & Co. KG) | 10 wt % particle size: 30 to 60 μm 50 wt % particle size: 70 to 110 μm 90 wt % particle size: 110 to 150 μm (measured by particle size analysis-laser diffraction methods) |

Examples 1 to 6

The crystalline hydrate form obtained in Production Example 1 (hereinafter referred to as "medicinal component" (the same also applies to Examples 7 to 43 below)) was ground by jet milling (A-O JET MILL, SEISHIN ENTERPRISE Co., Ltd.) so that six ground products having different particle size distributions were obtained. Subsequently, 2,800 g of Lactose 1 and 400 g of Lactose 2 were physically mixed in a V-type mixer (Kotobuki Mix Well VY-10&5&3, Tokuju Corporation). To 1.2 g of the resulting lactose mixture powder was added 0.3 g of each of the six ground products of the medicinal component and physically mixed in a Turbula mixer (TURBULA, Willy A. Bachofen AG, Switzerland), so that pharmaceutical compositions of Examples 1 to 6 were obtained. Table 2 shows the 10% by weight particle size, 50% by weight particle size, and 90% by weight particle size of the ground product of the medicinal component in each of the pharmaceutical compositions as measured by particle size analysis-laser diffraction methods.

TABLE 2

| | | Particle size of medicinal component (μm) (measured by particle size analysis-laser diffraction methods) | | |
|---|---|---|---|---|
| | | 10 wt % particle size | 50 wt % particle size | 90 wt % particle size |
| Example 1 | Medicinal component 1 | 0.86 | 2.61 | 6.20 |
| Example 2 | Medicinal component 2 | 0.80 | 2.08 | 4.63 |
| Example 3 | Medicinal component 3 | 0.78 | 1.91 | 4.04 |
| Example 4 | Medicinal component 4 | 0.91 | 2.92 | 6.97 |
| Example 5 | Medicinal component 5 | 1.09 | 3.64 | 8.87 |
| Example 6 | Medicinal component 6 | 0.97 | 3.26 | 7.93 |

Examples 7 to 26

The crystalline hydrate form (medicinal component) obtained in Production Example 1 was ground by jet milling so that ground products having the particle size distributions shown in Table 3 were obtained, respectively. Different diluting agents were added in the ratio shown in Table 4 or 5 to the ground product so that the content of the medicinal component was 20% by weight on anhydrous basis and that the total weight was 10 g. They were physically mixed in a Turbula mixer so that each of pharmaceutical compositions of Examples 7 to 26 was obtained.

<Particle Size Distributions of the Ground Products of Medicinal Component Added in Examples 7 to 26>

TABLE 3

| | Particle size (μm) of medicinal component (measured by particle size analysis-laser diffraction methods) | | |
|---|---|---|---|
| | 10 wt % particle size | 50 wt % particle size | 90 wt % particle size |
| Medicinal component 7 | 0.86 | 2.61 | 6.20 |
| Medicinal component 8 | 0.80 | 2.29 | 5.88 |

TABLE 4

| Example | 7 | 8 | 9 | 10 | 11 | 12 | 13 | 14 | 15 |
|---|---|---|---|---|---|---|---|---|---|
| Medicinal component 7 | 20*1 | ← | ← | ← | ← | ← | ← | ← | ← |
| Lactose 1 | 70*2 | 60*2 | 50*2 | 40*2 | 60*2 | | | | |
| Lactose 2 | 10*2 | 20*2 | 30*2 | 40*2 | 10*2 | | | | |
| Lactose 3 | | | | | | 80*2 | 70*2 | | |
| Lactose 4 | | | | | | | | 80*2 | 70*2 |
| Lactose 5 | | | | | 10*2 | | 10*2 | | 10*2 |

*1 The number indicates the content (% by weight on anhydrous basis) of the medicinal component in the pharmaceutical composition.
*2 The number indicates the relative weight ratio between the additives.

TABLE 5

| Example | 16 | 17 | 18 | 19 | 20 | 21 | 22 | 23 | 24 | 25 | 26 |
|---|---|---|---|---|---|---|---|---|---|---|---|
| Medicinal component 7 | 20*1 | ← | ← | ← | ← | ← | ← | | | | |
| Medicinal component 8 | | | | | | | | ← | ← | ← | ← |
| Lactose 1 | 70*2 | 70*2 | 69.1*2 | 65.6*2 | 68.2*2 | 69.1*2 | 70*2 | 70*2 | 69.1*2 | 65.6*2 | 65.6*2 |
| Lactose 2 | 10*2 | 10*2 | 9.9*2 | 9.4*2 | 9.8*2 | 9.9*2 | 10*2 | 10*2 | 9.9*2 | 9.4*2 | 9.4*2 |
| Magnesium stearate | 0.1*2 | 0.5*2 | | | | | | | | | |
| Ground L-leucine | | | 1*2 | 5*2 | | | | | | | |
| Light anhydrous silicic acid | | | | | 2*2 | 1*2 | 0.5*2 | | | | |
| Calcium stearate | | | | | | | | 0.5*2 | | | |
| Sodium stearyl fumarate | | | | | | | | | 1*2 | 5*2 | |
| Sucrose stearate | | | | | | | | | | | 5*2 |

*1 The number indicates the content (% by weight on anhydrous basis) of the medicinal component in the pharmaceutical composition.
*2 The number indicates the relative weight ratio between the additives.

Examples 27 to 34

The crystalline hydrate form (medicinal component) obtained in Production Example 1 was ground by jet milling so that a ground product (Medicinal component 9) having the particle size distribution shown in Table 6 was obtained. Different diluting agents were added in the ratio shown in Table 7 to the ground product, and they were physically mixed in a Turbula mixer so that each of pharmaceutical compositions of Examples 27 to 34 was obtained.

<Particle Size Distribution of the Ground Product of Medicinal Component Added in Examples 27 to 34>

TABLE 6

| | Particle size (μm) of medicinal component (measured by particle size analysis-laser diffraction methods) | | |
|---|---|---|---|
| | 10 wt % particle size | 50 wt % particle size | 90 wt % particle size |
| Medicinal component 9 | 0.94 | 2.90 | 7.28 |

TABLE 7

| Example | 27 | 28 | 29 | 30 | 31 | 32 | 33 | 34 |
|---|---|---|---|---|---|---|---|---|
| Medicinal component 9 | 20*1 | ← | ← | ← | ← | 10*1 | 30*1 | 50*1 |
| Lactose 1 | 80*2 | | | 70*2 | 60*2 | 70*2 | 70*2 | 70*2 |
| Lactose 2 | | | | 10*2 | 20*2 | 10*2 | 10*2 | 10*2 |
| Lactose 6 | | 80*2 | | | | | | |
| Lactose 7 | | | 80*2 | | | | | |

*1 The number indicates the content (% by weight on anhydrous basis) of the medicinal component in the pharmaceutical composition.
*2 The number indicates the relative weight ratio between the additives.

Example 35

The crystalline hydrate form (medicinal component) obtained in Production Example 1 was ground by jet milling so that a ground product having the particle size distribution shown in Table 8 was obtained. Subsequently, 8,400 g of Lactose 1 and 1,200 g of Lactose 2 were sieved with a granulator (COMIL QC-U-10, POWREX CORPORATION) and then physically mixed in a V-type mixer (TCV-60, Tokuju Corporation) to form a lactose mixture powder. The lactose mixture powder was added to the ground product of the medicinal component so that the content of the medicinal component was 20% by weight on an anhydrous basis. They were sieved with a granulator (COMIL QC-U-10, POWREX CORPORATION) and then physically mixed in a V-type mixer (TCV-60, Tokuju Corporation) to form 4,000 g of a pharmaceutical composition of Example 27. The manufacturing process was performed in an environment with a controlled temperature in the range of 19° C. to 27° C. and a controlled relative humidity in the range of 30% RH to 65% RH.

TABLE 8

| | Particle size distribution (μm) of the ground product of medicinal component (measured by particle size analysis-laser diffraction methods) | | |
|---|---|---|---|
| | 10 wt % particle size | 50 wt % particle size | 90 wt % particle size |
| Example 35 | 0.87 | 2.66 | 6.89 |

Examples 36 to 40

The crystalline hydrate form (medicinal component) obtained in Production Example 1 was ground by jet milling so that five ground products having the particle size distributions shown in Table 9 were obtained. Subsequently, 8,400 g of Lactose 1 and 1,200 g of Lactose 2 were sieved with a granulator (COMIL QC-U-10, POWREX CORPORATION) and then physically mixed in a V-type mixer (TCV-60, Tokuju Corporation) to form a lactose mixture powder. The lactose mixture powder was added to the ground product of the medicinal component so that the content of the medicinal component was 20% by weight on an anhydrous basis. They were sieved with a granulator (COMIL QC-U-10, POWREX CORPORATION) and then physically mixed in a V-type mixer (TCV-60, Tokuju Corporation) to form 3,000 g of each of pharmaceutical compositions of Examples 28 to 32. The manufacturing process was performed in an environment with a controlled temperature in the range of 19° C. to 27° C. and a controlled relative humidity in the range of 30% RH to 65% RH.

TABLE 9

| | Particle size distribution (μm) of the ground product of medicinal component (measured by particle size analysis-laser diffraction methods) | | |
|---|---|---|---|
| | 10 wt % particle size | 50 wt % particle size | 90 wt % particle size |
| Example 36 | 0.83 | 2.49 | 6.51 |
| Example 37 | 0.85 | 2.57 | 6.68 |
| Example 38 | 0.85 | 2.49 | 6.36 |
| Example 39 | 0.94 | 2.90 | 7.28 |
| Example 40 | 0.98 | 2.92 | 7.16 |

Example 41

The crystalline hydrate form (medicinal component) obtained in Production Example 1 was ground by jet milling so that a ground product having the particle size distribution shown in Table 10 was obtained. Subsequently, 5,600 g of Lactose 1 and 800 g of Lactose 2 were sieved by hand sieving and then physically mixed in a V-type mixer (TCV-10, Tokuju Corporation) to form a lactose mixture powder. The lactose mixture powder was added to the ground product of the medicinal component so that the content of the medicinal component was 20% by weight on anhydrous basis. They were sieved by hand sieving and then physically mixed in a V-type mixer (TCV-10, Tokuju Corporation) to form 1,600 g of a pharmaceutical composition of Example 41. The manufacturing process was performed in an environment with a controlled temperature in the range of 19° C. to 27° C. and a controlled relative humidity in the range of 30% RH to 65% RH.

Example 42

The crystalline hydrate form (medicinal component) obtained in Production Example 1 was ground by jet milling so that a ground product having the particle size distribution shown in Table 10 was obtained. Subsequently, 5,600 g of Lactose 1 and 800 g of Lactose 2 were sieved with a granulator (COMIL QC-U-10, POWREX CORPORATION) and then physically mixed in a V-type mixer (TCV-10, Tokuju Corporation) to form a lactose mixture powder. The lactose mixture powder was added to the ground product of the medicinal component so that the content of the medicinal component was 20% by weight on an anhydrous basis. They were sieved with a granulator (COMIL QC-U-10, POWREX CORPORATION) and then physically mixed in a V-type mixer (TCV-10, Tokuju Corporation) to form 2,000 g of a pharmaceutical composition of Example 42. The manufacturing process was performed in an environment with a controlled temperature in the range of 19° C. to 27° C. and a controlled relative humidity in the range of 30% RH to 65% RH.

Example 43

The crystalline hydrate form (medicinal component) obtained in Production Example 1 was ground by jet milling so that three ground products having the particle size distributions shown in Table 10 were obtained. Subsequently, 6,000 g of Lactose 1 and 1,000 g of Lactose 2 were sieved with a granulator (COMIL QC-U-10, POWREX CORPORATION) and then physically mixed in a V-type mixer (TCV-60, Tokuju Corporation) to form a lactose mixture powder. The lactose mixture powder was added to the ground product of the medicinal component so that the content of the medicinal component was 20% by weight on an anhydrous basis. They were sieved with a granulator (COMIL QC-U-10, POWREX CORPORATION) and then physically mixed in a V-type mixer (TCV-60, Tokuju Corporation) to form 3,000 g of a pharmaceutical composition of Example 43. The manufacturing process was performed in an environment with a controlled temperature in the range of 19° C. to 27° C. and a controlled relative humidity in the range of 30% RH to 65% RH.

TABLE 10

| | Particle size distribution (μm) of the ground product of medicinal component (measured by particle size analysis-laser diffraction methods) | | |
|---|---|---|---|
| | 10 wt % particle size | 50 wt % particle size | 90 wt % particle size |
| Example 41 | 0.83 | 2.48 | 6.33 |
| Example 42 | 0.80 | 2.32 | 5.94 |
| Example 43 | 0.83 | 2.48 | 6.29 |

Test Example 1

Evaluation of the Ability of Drug to Reach Respiratory System (Examining the Link Between Main Drug Particle Size and FPF)

A method of measuring the amount of fine particles using a cascade impactor is generally used as a simple method of evaluating in vitro the ability of an inhalant to reach the respiratory system (see for example USP 31, <601> Aerosol/Physical Tests and European Pharmacopoeia 5.2, 2.9.18 Preparations for inhalation: Aerodynamic Assessment of Fine Particles).

This method uses an apparatus for classifying drug particles, in which the drug particles are introduced by suction into the cascade impactor using a pump from an inhaler. The drug particles being introduced reach any of 12 parts of the cascade impactor (mouthpiece adapter, pre-separator, induction port, stages 0 to 7, and filter) depending on the particle size. Large particles such as diluting agent particles, drug particles not released from the diluting agent, and aggregates are collected at the mouthpiece adapter, pre-separator and induction port. The drug particles released from the diluting agent reach any of stages 0 to 7 and the filter, in which the smaller-sized particles reach the larger-number stage, and the drug particles passing through stage 7 are collected at the filter.

It is known that the amount of the drug reaching a specific part or the proportion of the amount in the indicated amount correlates with the ability of the drug to reach the respiratory system in clinical use (see for example USP 31, <601> Aerosol/Physical Tests). The former is referred to as Fine Particle Dose (hereinafter referred to as FPD), and the latter is called Fine Particle Fraction (hereinafter referred to as FPF). Concerning the indicated amounts of the pharmaceutical composition of the present invention, FPD is defined as the amount of the drug reaching the parts from stage 3 to the filter, and FPF is defined as the proportion of FPD in the indicated amount. The ability to reach the respiratory system was evaluated using these parameters.

Table 11 shows the FPF values of Examples 1 to 6 prepared with ground products of the medicinal component having different particle size distributions.

Examples 1 to 4 in which the medicinal component had a 50% by weight particle size of 3.2 μm or less as measured by particle size analysis-laser diffraction methods showed higher FPF values than Example 5 or 6 with a 50% by weight particle size of 3.2 μm or more.

TABLE 11

| Example | | FPF (%) |
|---|---|---|
| 1 | Medicinal component 1 | 43.3 |
| 2 | Medicinal component 2 | 40.0 |
| 3 | Medicinal component 3 | 45.0 |
| 4 | Medicinal component 4 | 35.8 |
| 5 | Medicinal component 5 | 30.2 |
| 6 | Medicinal component 6 | 29.1 |

Test Example 2

FPF and Spray Efficiency for Different Diluting Agent Compositions

The reproducibility of the dose sprayed from an inhaler (the uniformity of the sprayed dose) is one of the basic formulation properties of an inhalant. The United States Pharmacopoeia (hereinafter referred to as USP) describes a method that includes spraying a drug into a special chamber from an inhaler using a pump and determining the proportion (spray efficiency) of the amount of the sprayed drug in the indicated amount (see USP 31, <601> Aerosol/Physical Tests). The spray efficiency (%) of the pharmaceutical composition of the present invention was evaluated according to the USP method.

Table 12 shows the FPF and spray efficiency of some of the pharmaceutical compositions of Examples 7 to 26 shown in Tables 4 and 5, which are different in diluting agent composition. All the examples showed an FPF of 30% or more and a spray efficiency of 70% or more, which indicated that the dosage form could efficiently deliver the compound of formula (I) to the respiratory system.

TABLE 12

| Example | FPF (%) n = 1 | Spray efficiency (%) n = 5 mean ± SD |
|---|---|---|
| 7 | 38.1 | 70.0 ± 11.7 |
| 10 | 36.2 | 76.7 ± 6.6 |
| 17 | 30.2 | 73.0 ± 7.9 |
| 19 | 34.6 | 77.6 ± 5.6 |
| 21 | 36.9 | 82.8 ± 5.2 |
| 22 | 37.6 | 78.6 ± 2.6 |

Test Example 3

Relationship Between the Particle Size, Blend Ratio of Lactose and the Medicinal Component Concentration and FPD Table 13 shows FPD for the pharmaceutical compositions of Examples 27 to 34 shown in Tables 7 and 8. Concerning the particle size and blend ratio of lactose, the pharmaceutical compositions with a weight blend ratio of Lactose 1 and Lactose 2 from 0:100 to 60:20 and a medicinal component concentration of 10 to 30% by weight showed high FPD.

TABLE 13

| Example | FPD (mg) n = 3 |
|---|---|
| 27 | 6.0 |
| 28 | 5.4 |
| 29 | 3.6 |
| 30 | 6.6 |
| 31 | 7.1 |
| 32 | 6.1 |
| 33 | 5.5 |
| 34 | 3.6 |

Test Example 4

Test of Comparison with Oseltamivir Phosphate for Adult Patients

The subjects were adult patients (20 or more years old) with influenza A or B virus infection. The crystalline hydrate form (medicinal component) obtained in Production Example 1 was administered in a single inhaled dose to the subjects. The efficacy of the medicinal component was evaluated from non-inferiority to oseltamivir phosphate using the duration of influenza illness as the main evaluation item. The administration was performed using the composition prepared with the medicinal component, Lactose 1 and Lactose 2 according to Example 43. The administration was performed so that the dose of the medicinal component was 20 mg or 40 mg on anhydrous basis. Based on the dose of the medicinal component, the pharmaceutical composition of the present invention prepared in such a manner is referred to as "medicinal component 20 mg", "medicinal component 40 mg", or the like. The same applies to Test Examples 5 to 8 below.

Oseltamivir phosphate was repeatedly administered in a dose of 75 mg twice daily for 5 days.

This test was a non-inferiority test in which the efficacy of the medicinal component was confirmed by showing that the duration of influenza illness for the effect of the medicinal component is not 18 hours longer than that for the effect of oseltamivir phosphate. When the upper limit of the 95% confidence interval for the difference between the median values of each medicinal component administration group and the oseltamivir phosphate group was less than 18 hours, it was decided that the medicinal component was an effective therapeutic agent for influenza virus infections. For multiplicity control, the decision was sequentially made in decreasing order of dose.

Table 14 shows the median value of the duration of influenza illness at each dose level of the medicinal component, and Table 15 shows the difference (95% confidence interval) in median value from the oseltamivir phosphate group.

TABLE 14

| | Median value (hours) of the duration of influenza illness |
|---|---|
| Medicinal component 20 mg group | 85.8 |
| Medicinal component 40 mg group | 73.0 |
| Oseltamivir phosphate group | 73.6 |

The duration of the illness was slightly longer in the medicinal component 20 mg group than in the oseltamivir phosphate group, while the duration in the medicinal component 40 mg group was almost equal to that in the oseltamivir phosphate group.

TABLE 15

| | Difference (95% confidence interval, hours) in median value from the oseltamivir phosphate group |
|---|---|
| Medicinal component 20 mg group | 12.2(−1.5 to 17.2) |
| Medicinal component 40 mg group | −0.6(−9.9 to 6.9) |

Concerning the difference (95% confidence interval) in median value from the oseltamivir phosphate group, the upper limit of the 95% confidence interval for the difference between the median values was less than 18 hours for every dose group.

Thus it was demonstrated that the effect of a single inhaled dose of medicinal component 20 mg or 40 mg was comparable to that of the oseltamivir phosphate administration in a dose of 75 mg twice daily for 5 days and that the medicinal component was an effective therapeutic agent for influenza infections.

Test Example 5

Test of Comparison with Oseltamivir Phosphate for Child Patients

The subjects were child patients (9 or less years old) with influenza A or B virus infection. The medicinal component was administered in a single inhaled dose of 20 mg or 40 mg. The efficacy of the medicinal component was evaluated by comparison with oseltamivir phosphate using the duration of influenza illness as the main evaluation item.

The administration was performed using the composition prepared according to Example 43.

For the evaluation of efficacy, a three-group, randomized, double-blind, comparison test was performed using oseltamivir phosphate as a control.

Oseltamivir phosphate was repeatedly administered in a dose of 2 mg/kg (on body weight basis) twice daily for 5 days.

Table 16 shows the median value of the duration of influenza illness at each dose level of the medicinal component, and Table 17 shows the difference (95% confidence interval) in median value from the oseltamivir phosphate group.

TABLE 16

| | Median value (hours) of the duration of influenza illness |
|---|---|
| Medicinal component 20 mg group | 56.4 |
| Medicinal component 40 mg group | 55.4 |
| Oseltamivir phosphate group | 87.3 |

TABLE 17

| | Difference (95% confidence interval, hours) in median value from the oseltamivir phosphate group |
|---|---|
| Medicinal component 20 mg group | −31.0(−50.3 to −5.5) |
| Medicinal component 40 mg group | −31.9(−43.4 to 0.5) |

The duration of the illness was shorter in each of the medicinal component 20 mg group and the medicinal component 40 mg group than in the oseltamivir phosphate group (generalized Wilcoxon test: P=0.0099 (medicinal component 20 mg group), P=0.0591 (medicinal component 40 mg group)).

Thus it was demonstrated that the effects of a single inhaled dose of medicinal component 20 mg or 40 mg were superior to that of oseltamivir phosphate and that the medicinal component was an effective therapeutic agent for influenza infections in children (9 or less years old).

Test Example 6

Test of Comparison with Oseltamivir Phosphate for Adult Patients

The subjects were patients with influenza A or B virus infection. The efficacy of the medicinal component administered in two inhaled doses of 20 mg each was evaluated by a two-group, randomized, double-blind, comparison test using oseltamivir phosphate as a control. For efficacy, the duration of influenza illness was used as the main evaluation item, and the relative levels of oseltamivir phosphate and the medicinal component administered in two inhaled doses of 20 mg each were evaluated.

The administration was performed using the composition prepared according to Example 42.

Oseltamivir phosphate was repeatedly administered in a dose of 75 mg twice daily for 5 days.

Table 18 shows the median value of the duration of influenza illness as the main evaluation item, and Table 19 shows the difference (95% confidence interval) in median value from the oseltamivir phosphate group.

TABLE 18

| | Median value (hours) of the duration of influenza illness |
|---|---|
| Medicinal component group | 86.0 |
| Oseltamivir phosphate group | 87.4 |

TABLE 19

| | Difference (95% confidence interval, hours) in median value from the oseltamivir phosphate group |
|---|---|
| Medicinal component group | −1.4(−27.6 to 7.3) |

The duration of influenza illness in the medicinal component group was almost equal to that in the oseltamivir phosphate group.

Thus it was suggested that two inhaled doses of medicinal component 20 mg each might be an effective regimen for influenza virus infections.

Test Example 7

Test for Evaluation of Pharmacokinetics in Healthy Adult Male Subjects

The medicinal component was administered in a single inhaled dose of 5 mg, 10 mg, 20 mg, or 40 mg to healthy adult male subjects, and the pharmacokinetics of the medicinal component and the compound (III), which is an active metabolite of the medicinal component, were evaluated.

The administration was performed using the composition prepared according to Example 41.

Upon the administration of the medicinal component in a single inhaled dose, the medicinal component and the compound (III), an active metabolite of the medicinal component, were detected in the plasma and the urine. In each dose group, the concentration of the medicinal component in the plasma quickly increased and then decreased to less than the quantification lower limit 24 hours or more after the administration. The concentration of the active metabolite compound (III) in the plasma increased more slowly than the medicinal component, and then attenuated. In the maximum dose (40 mg) group, the compound (III) was able to be quantified until the final measurement point 144 hours after the administration, and it had an elimination half-life ($t_{1/2}$) of 63.99 hours.

For the urinary excretion, the medicinal component was almost not detected 24 hours or more after the administration. The active metabolite compound (III) was sustained until 144 hours after the administration. The elimination half-life of the active metabolite compound (III) calculated from the in-urine excretion speed was 54.36 to 64.05 hours.

Dose proportionality was observed for each of the maximum blood concentration ($C_{max}$) of the medicinal component, the value of the area under the plasma concentration-time curve to the final quantifiable point ($AUC_{0-tz}$) for the medicinal component, the value of the area under the plasma concentration-time curve to infinite time ($AUC_{0-inf}$) for the medicinal component, the cumulative urinary excretion until 144 hours after the administration ($Ae_{0-144h}$) for the medicinal component, and the $C_{max}$ and the $Ae_{0-144h}$ of the active metabolite compound (III).

The pharmacokinetic results showed that a single dose of the medicinal component produced systemic exposure that accompanies the increase of dose, and had the potential to exhibit long-lasting activity.

Test Example 8

Test for Evaluation of Pharmacokinetics in Healthy Adult Male Subjects (High Doses)

The medicinal component was administered in a single inhaled dose of 80 mg or 120 mg to healthy adult male subjects, and the pharmacokinetics of the medicinal component were evaluated. In addition, the pharmacokinetics of the Compound (III), an active metabolite of the medicinal component, were also determined.

The administration was performed using the composition prepared according to Example 41.

Table 16 shows the results on the time to maximum plasma concentration ($t_{max}$, median), the elimination half-life ($t_{1/2}$, geometric mean), the maximum blood concentration ($C_{max}$, geometric mean), the value of the area under the plasma concentration-time curve to infinite time ($AUC_{0-inf}$, geometric mean), and the cumulative urinary recovery until 144 hours after the administration ($fe_{0-144h}$, geometric mean).

It was demonstrated that each dose produced systemic exposure that accompanies the increase in dose, and had the potential to exhibit long-lasting activity.

TABLE 20

|  | 80 mg group | | 120 mg group | |
| --- | --- | --- | --- | --- |
|  | medicinal component | Active metabolite | medicinal component | Active metabolite |
| $t_{max}$ [hr] | 0.5 | 4.0 | 0.5 | 4.0 |
| $t_{1/2}$ [hr] | 5.66 | 79.53 | 2.87 | 71.17 |
| $C_{max}$ [ng/mL] | 335.0 | 47.0 | 411.7 | 64.8 |
| $AUC_{0-inf}$ [ng/mL] | 1273 | 1996 | 1557 | 2531 |
| $fe_{0-144h}$ [%] | 3.5 | 14.2 | 2.7 | 12.5 |

The invention claimed is:

1. A dry powder pharmaceutical composition for inhalation comprising a mixture of (a) a medicinal component which is a mixture of (i) a compound of the following formula (I):

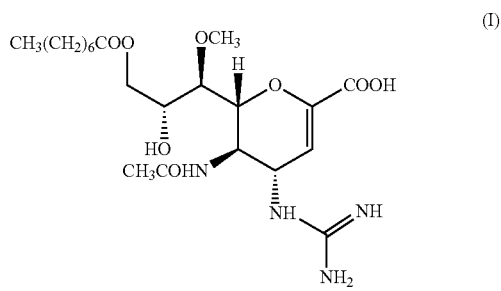

a pharmaceutically acceptable salt thereof, or a hydrate thereof,
and (ii) a compound of the following formula (II):

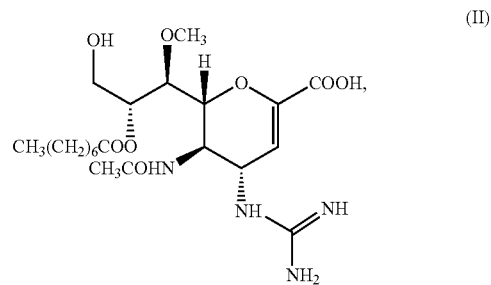

a pharmacologically acceptable salt thereof, or a hydrate thereof, and (b) a diluting agent comprising a mixture of a first lactose hydrate and a second lactose hydrate which have different particle size distributions, wherein the medicinal component has a 50% by weight particle size of 3.2 μm or less and a 90% by weight particle size of 8.0 μm or less as measured by a particle size analysis-laser diffraction method, and having 15% to 25% by weight on an anhydrous basis of the medicinal component,
   wherein the first lactose hydrate has a particle size distribution satisfying the following condition: the particle size distribution of the first lactose hydrate measured by a particle size analysis-laser diffraction method has
   a 10% by weight particle size of 19 μm to 43 μm,
   a 50% by weight particle size of 53 μm to 66 μm, and
   a 90% by weight particle size of 75 μm to 106 μm,
   and the second lactose hydrate satisfying the following condition: the particle size distribution of the second lactose hydrate measured by a particle size analysis-laser diffraction method has
   a 10% by weight particle size of 1 μm to 3 μm,
   a 50% by weight particle size of 11 μm to 20 μm, and
   a 90% by weight particle size of 37 μm to 54 μm.

2. The dry powder pharmaceutical composition for inhalation according to claim 1, wherein the medicinal component is prepared by a microparticulation process selected from the group consisting of (a) a dry pulverization process which is selected from the group consisting of (i) a jet milling process and (ii) a pin milling process, (b) a wet pulverization process, (c) a spray-drying process and (d) a freeze-drying process.

3. The dry powder pharmaceutical composition for inhalation according to claim 1, wherein the microparticulation process of the medicinal component is a jet milling process.

4. The dry powder pharmaceutical composition for inhalation according to claim 1, comprising 20% by weight, on an anhydrous basis, of the medicinal component.

5. The dry powder pharmaceutical composition for inhalation according to claim 1, which is manufactured by a method selected from the group consisting of a physical mixing method, a spray-drying method and a freeze-drying method.

6. The dry powder pharmaceutical composition for inhalation according to claim 1, which is manufactured by a physical mixing method.

7. The dry powder pharmaceutical composition for inhalation according to claim 1, which contains 5 to 120 mg of the medicinal component on an anhydrous basis.

8. The dry powder pharmaceutical composition for inhalation according to claim 7, wherein the composition is provided as a single dose or two divided doses.

9. The dry powder pharmaceutical composition for inhalation according to claim 1, wherein the compound of formula (I) is in a form of a crystalline hydrate, and the compound of formula (II) is in a form of a crystalline hydrate.

10. The dry powder pharmaceutical composition for inhalation according to claim 1, wherein the compound of formula (I) is in a form of a crystalline monohydrate, and the compound of formula (II) is in a form of a crystalline monohydrate.

11. The dry powder pharmaceutical composition for inhalation according to claim 1, wherein the medicinal component consists of a mixture of a crystalline monohydrate form of the compound of formula (I) and a crystalline monohydrate form of the compound of formula (II).

12. The dry powder pharmaceutical composition for inhalation according to claim 11, wherein the % by weight on an anhydrous basis of the medicinal component is 20%.

13. The dry powder pharmaceutical composition for inhalation according to claim 1, which consists of the medicinal component, the first lactose hydrate and the second lactose hydrate.

14. A method for treating an influenza virus infection which comprises administering by inhalation a pharmaceutically effective amount of the dry powder pharmaceutical composition for inhalation according to claim 1 to a patient in need thereof.

15. The method according to claim 14, wherein the composition is administered in a single inhaled dose containing 20 mg of the medicinal component on an anhydrous basis.

16. The method according to claim 14, wherein the composition is administered in two inhaled doses containing 20 mg each of the medicinal component on an anhydrous basis.

17. The method according to claim 14, wherein the composition is administered in a single inhaled dose containing 40 mg of the medicinal component on an anhydrous basis.

18. The method according to claim 14, wherein the composition is administered in a single inhaled dose containing 80 mg of the medicinal component on an anhydrous basis.

19. The method according to claim 14, wherein the patient is a human.

20. The method according to claim 19, wherein the dry powder composition is administered as a single dose or two divided doses after an onset of an influenza virus infection, and the medicinal component is contained in an amount of 5 to 120 mg on an anhydrous basis.

* * * * *